(12) United States Patent
Elsener

(10) Patent No.: US 7,146,667 B2
(45) Date of Patent: Dec. 12, 2006

(54) POCKET TOOL

(75) Inventor: Carl Elsener, Ibach (CH)

(73) Assignee: Victorinox AG, Ibach (CH)

( * ) Notice: Subject to any disclaimer, the term of this patent is extended or adjusted under 35 U.S.C. 154(b) by 0 days.

(21) Appl. No.: 10/965,638

(22) Filed: Oct. 14, 2004

(65) Prior Publication Data

US 2005/0081302 A1 Apr. 21, 2005

(30) Foreign Application Priority Data

Oct. 17, 2003 (AT) ............................. A 1650/2003

(51) Int. Cl.
  *B26B 11/00* (2006.01)
(52) U.S. Cl. .............................................. 7/118; 7/170
(58) Field of Classification Search .................... 7/118, 7/158, 170; 81/177.4; 365/200
  See application file for complete search history.

(56) References Cited

U.S. PATENT DOCUMENTS

| | | | | |
|---|---|---|---|---|
| 4,854,045 A | * | 8/1989 | Schaub | 30/155 |
| 6,273,582 B1 | * | 8/2001 | Taggart et al. | 362/119 |
| 6,341,423 B1 | * | 1/2002 | Taggart et al. | 30/169 |
| 6,394,813 B1 | * | 5/2002 | Stout et al. | 439/11 |
| 6,561,421 B1 | * | 5/2003 | Yu | 235/451 |
| 6,675,419 B1 | * | 1/2004 | Rivera | 7/128 |
| 2004/0080989 A1 | * | 4/2004 | Yu | 365/200 |

FOREIGN PATENT DOCUMENTS

JP 2003 - 10570 1/2003

* cited by examiner

*Primary Examiner*—David B. Thomas
(74) *Attorney, Agent, or Firm*—Fross Zelnick Lehrman & Zissu, P.C.; Philip T. Shannon, Esq.; Charles T. J. Weigell, Esq.

(57) ABSTRACT

The invention specifies a pocket tool, particularly a pocket knife (1) or plate-like tool card, comprising a housing (2) with at least one receiving area (10), and at least two functional components (11) movable from a storage position within the receiving area (10), into a working position outside of the receiving area (10). The first functional component (11) is designed as a tool, particularly a pair of scissors (16) or knife (1). The second functional component (11) has a support casing (25) and is equipped with a recordable and readable, nonvolatile memory, as well as with an interface (24). A releasable locking device and a longitudinal guide or pivot bearing are arranged between the support casing (25) of the second functional component (11) and the housing (2).

118 Claims, 14 Drawing Sheets

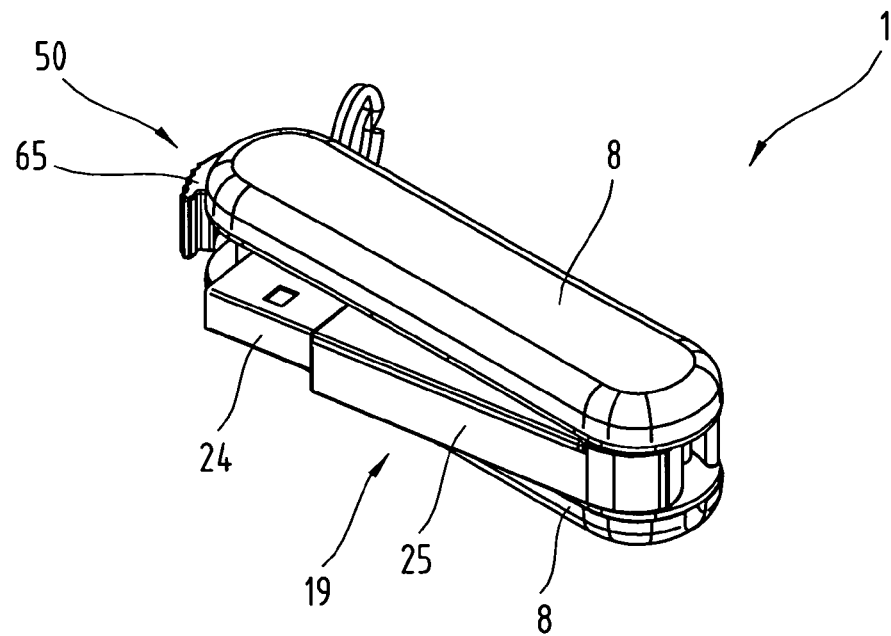
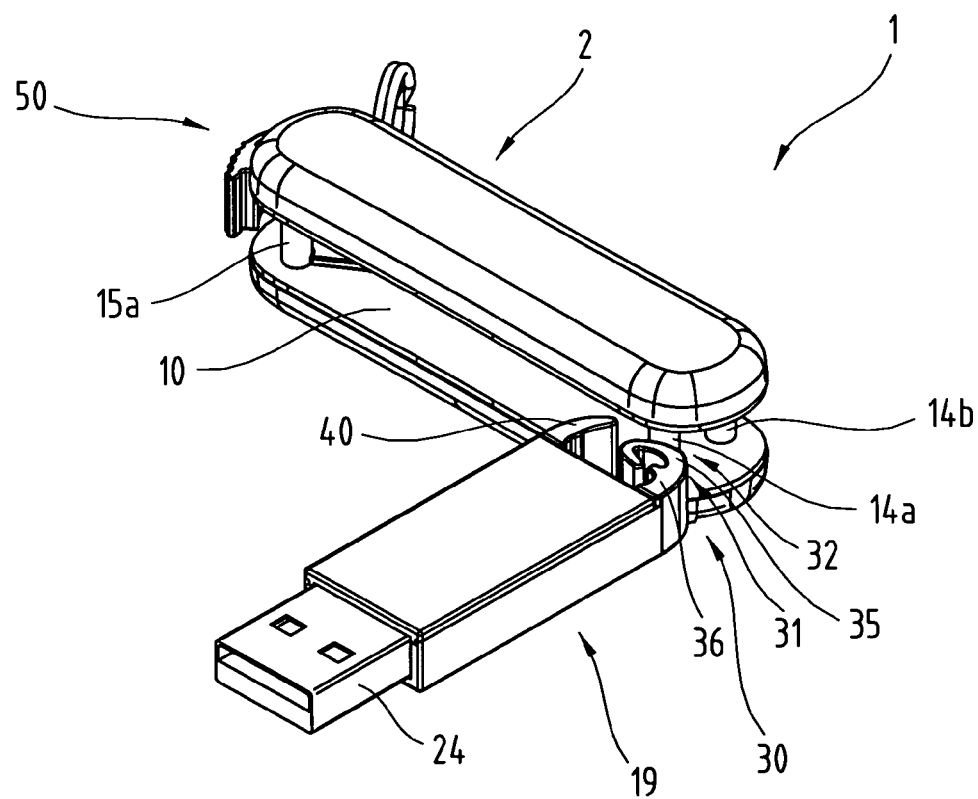

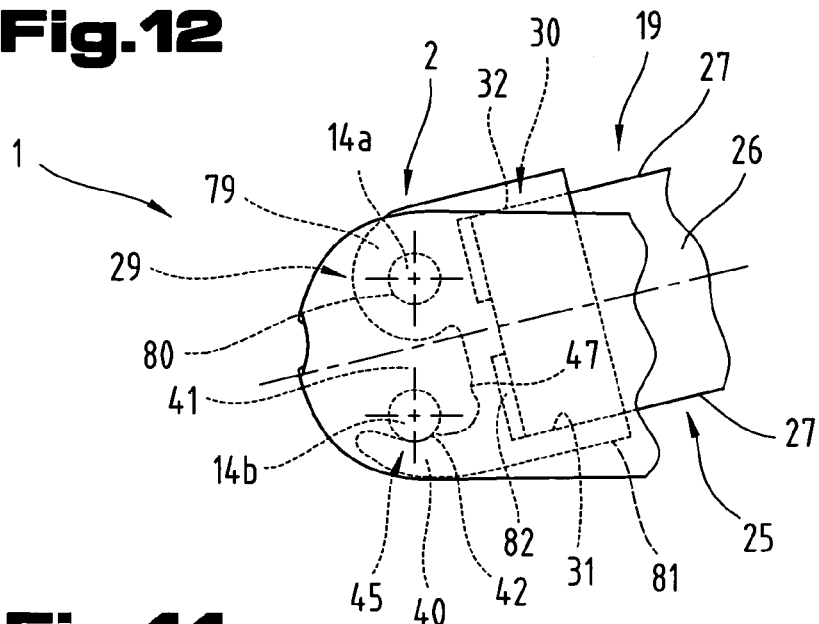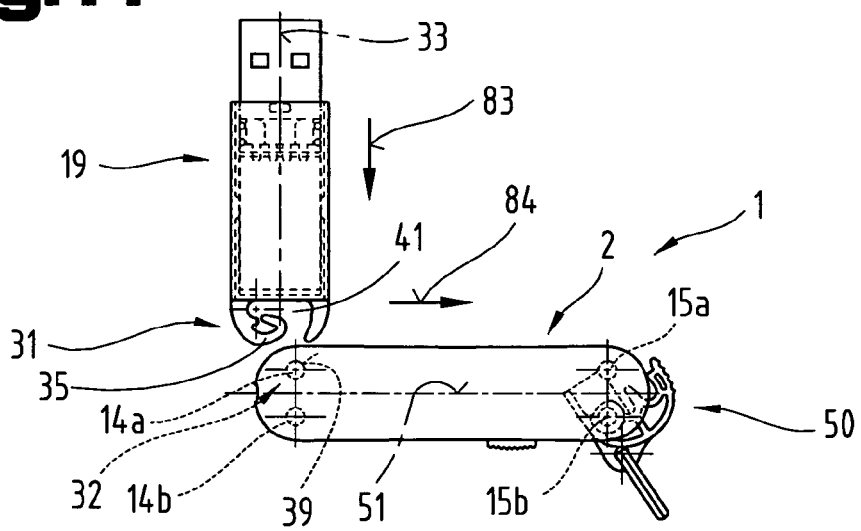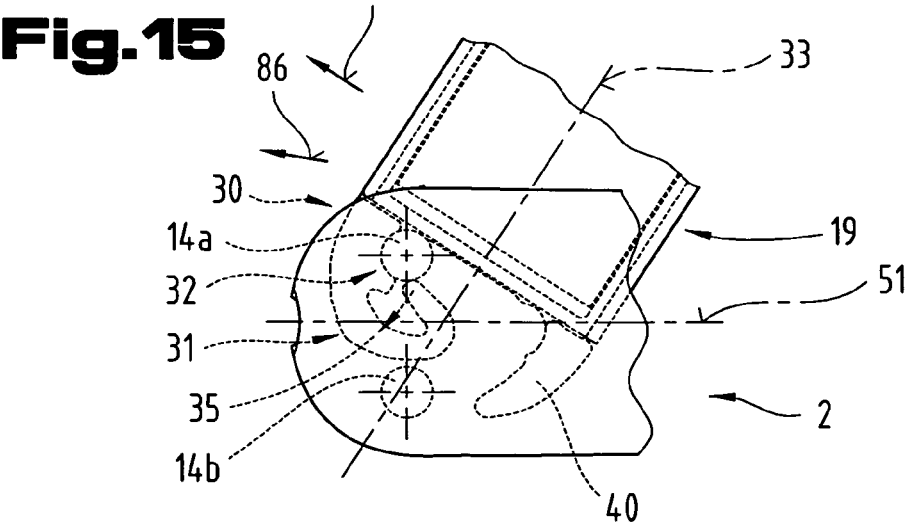

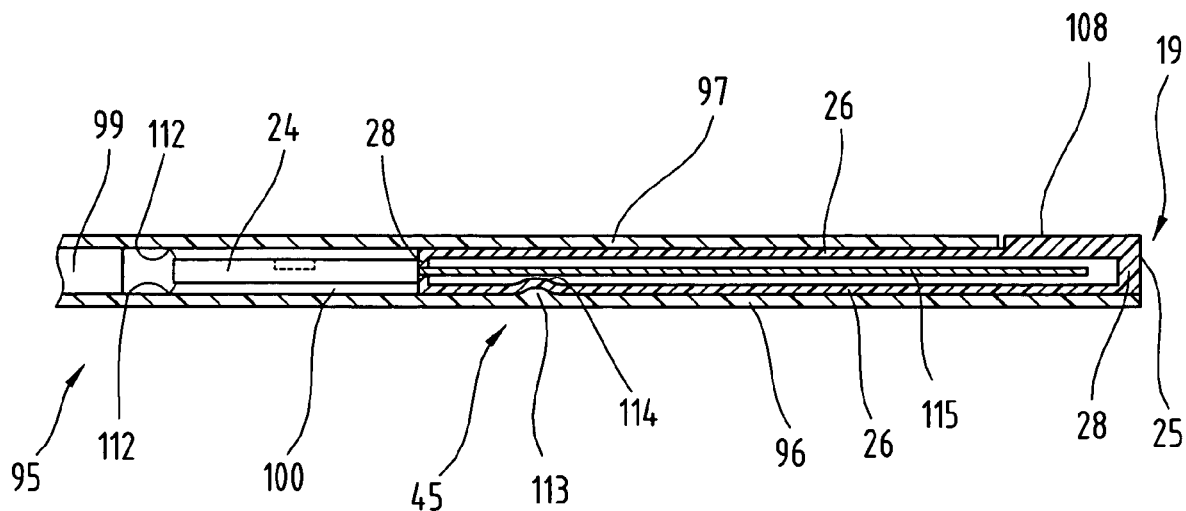
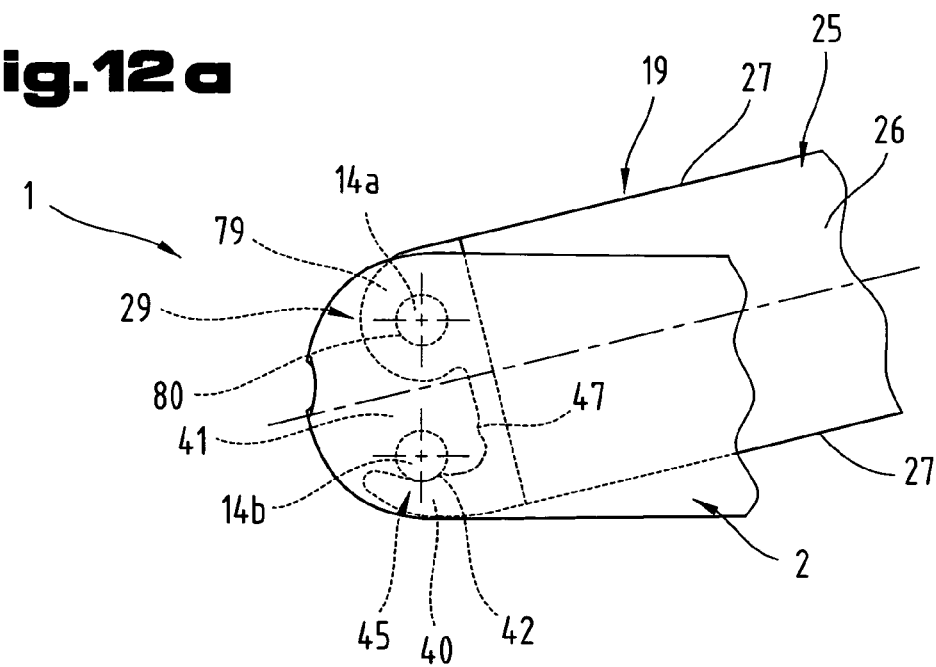

POCKET TOOL

CROSS REFERENCE TO RELATED APPLICATIONS

Applicant claims priority under 35 U.S.C. §119 of AUSTRIAN Patent Application No. A 1650/2003 filed on Oct. 17, 2003.

BACKGROUND OF THE INVENTION

1. Field of the Invention

The invention relates to a pocket tool as defined in the introductory parts of claims 1 and 44. Furthermore, it relates to a functional component as defined in the introductory part of claim 116.

2. The Prior Art

Different designs of pocket tools in the form of pocket knives or plate-shaped tool cards are known from WO 01/39629 A1 and CH 686 173 A5. Such tools comprise a housing with at least one receiving area and a number of functional components that are movable from a storage position within the receiving area, to a working position outside of the receiving area. On the one hand, such functional components are formed by tools such as, for example a pair of scissors, a knife, a screwdriver and the like, and by utensils such as, for example tooth picks, pincers or cleaning needles, on the other hand. The functionality of such known pocket tools is extended in that a battery-buffered random access memory (RAM) main memory, or a read-only memory (ROM) memory is arranged within the housing. Said memories are arranged locally fixed in the pocket knife. Programs or data can be stored in and recalled from such memories. The main memory is referred to also as a so-called volatile storage because it has to be supplied with the required voltage, so it will not lose the memory contents even if the supply voltage is shut off. Arranging the required battery in the housing leads to an overall enlargement of the size of the pocket tool, or that only a few functional components can be arranged in the housing with comparatively no change in the outside dimensions.

If the memory is designed as a ROM memory, data can only by read out from the memory; however, no data can be written into the memory, which means the user can exclusively utilize the data or programs preset by the manufacturer of the pocket tool, which highly restricts the field of application of such a pocket tool.

Furthermore, a multifunctional tool is known from WO 99/56918 A1, which has at least one measuring, input and display device for at least one physical quantity, said device being arranged in or on the tool. The display device may be formed in this connection by an LCD display serving for the visual output of physical quantities. The measuring and display device can be supplied with current by means of a battery and/or a solar cell. Furthermore, provision may be made in or on the tool for an interface in order to input data for the measuring and display device, and to transmit data from the latter. For converting the measured and/or input value into an electrical signal, provision can be made for a converter or microprocessor for converting the electrical signal into a standardized physical unit.

Such a multifunctional tool does in fact extend the functionality of a pocket knife or manual tool; however, the scope of functions is exclusively limited to the processing of detectable measured physical values.

The pocket tools known from the prior art are generally found to be lacking with respect to their capability of processing digital data and outputting the latter in a form the user can detect, so there is a demand for additionally extending the scope of functions of pocket tools, while maintaining at the same time in the usual manner the scope of functions to which the user is accustomed to, such functions being achievable with functional tools or components such as, e.g. screwdrivers, knifes, scissors, and utensils such as, e.g. toothpicks etc.

SUMMARY OF THE INVENTION

The present invention is based on the problem to extend the range of application of a pocket tool without influencing thereby the dimensions of the pocket tool as such. A part problem of the present invention consists in expanding the scope of functions and the range of application of the pocket tool with respect to its capability of processing digital data, the objective being to maintain the mechanical functionality through the availability of tools and utensils.

The problem of the invention is resolved by the features defined herein. The benefits resulting from said features include that the second functional component in the form of an electronic module can be moved for its application into a position outside of the receiving range of the pocket tool, achieving in this manner superior accessibility particularly to the interface. In the nonvolatile storage, it is possible to write in and read out data, for example text data or data as video and language information and the like, and programs, e.g. application programs and the like, whereby the nonvolatile storage is wherein contrary to the known volatile main memories, where data and programs can be read in and written out as well, the electrical energy supply can be dispensed with, and the space volume otherwise required for accommodating, e.g. a battery in the housing, can be used either as an additional storage space or for additional tools. The functionality of the pocket tools, and in particular the memory capacity or the range of application as a tool can be significantly raised in this way without substantially increasing its outside dimensions. It is advantageous also that a releasable locking device is arranged between the functional component and the housing, because any unintentional removal of the functional component from its storage position, for example, is excluded to the greatest possible extent. The longitudinal guide or pivot-mount between the support casing of the second functional component, and the housing of the pocket tool effect a smooth movement of the second functional component vis-à-vis the receiving area or a bearing axle arranged in the housing.

One embodiment is advantageous in that, on the one hand, the memory and the control circuit and/or at least one peripheral are arranged within the support casing, which is enclosed on all sides and consequently protected from environmental influences such as, e.g. moisture, dust and the like; and that the support casing has high mechanical stability and is insensitive to pressure stress, on the other hand. The interface represents a link between the memory and an external EDP system.

As disclosed, it is also possible to maintain a standardized length of a pocket tool known in the prior art.

Beneficial sequence activities for the second functional component are also disclosed.

Further developments of the invention are advantageous in that the second functional component forming the electronics module is, in its working position, now completely separated from the housing, and can be used independently of the latter. Particularly the increasingly stricter security regulations in airline traffic prohibit passengers from using a pocket tool in the passenger cabin of an aircraft, especially one with a knife blade or scissors and the like. Since it is now possible to separate the electronics module from the housing via the coupling device of the pivot mount, if necessary, the housing with the tools can be accommodated in the luggage of the traveler, whereas the electronics module can be carried on the user in the passenger cabin.

In one embodiment, the design is beneficial in that the bearing axle that is present in the housing, to begin with, is now forming the second component of the coupling; and that no additional structural components have to be arranged in the housing, which in turn would lead to larger outside dimensions of the pocket tool.

According to the further developments of the invention, the second component of the coupling is formed by an adapter pivot-mounted on the bearing axle in the housing, which means that the electronics module can be coupled with and uncoupled from the adapter in a particularly simple manner.

Other embodiments are beneficial as well in that the side walls and/or partitions, which are present in the basic structure of the pocket tool, to begin with, serve as longitudinal guides. In this connection, the electronics module can be inserted into the receiving area with the interface facing the latter first, in the direction extending parallel to the longitudinal axis of the pocket tool, and pulled out from the receiving area in the opposite direction in a guided manner. The receiving area is formed between two side walls facing one another, or between a side wall and a partition of the pocket knife, or between two partitions disposed next to each other, keeping the base and cover plates of a tool card spaced from each other.

Other embodiments offer a special advantage as well in that in its storage position, the electronics module can be locked within the receiving area via the locking device, which assures that it is fixed free of exposure to vibration. In a first design variation, the locking device is formed by plug or detent or snap elements, or elements of friction grip that can be engaged with each other. According to the design of the pocket tool in the form of a pocketknife, the plug or detent or snap elements are arranged in the housing on at least one of the two side surfaces of two adjacent side and/or partitions facing one another, and on the support casing on at least one of the walls on the broad and/or narrow sides. According to the tool card, the plug or detent or snap elements are arranged in the housing on at least one of the inner side surfaces of the base and cover plates facing one another, and/or on at least one of the partitions disposed adjacent to each other, and on the support casing on at least one of the side walls on the broad and/or narrow sides.

Different advantageous embodiments of the housing of the pocket tool are also disclosed. In a preferred embodiment of the pocket tool, the support casing of the electronics module is pivot-mounted on the bearing axle arranged in the housing, swiveling about an axis extending perpendicular to its broad-side walls, so that the width measured between the parallel broad-side walls determines the overall width of the pocket tool, and the height of the support casing of the electronics module substantially corresponds with the standardized overall height of the pocket tool. However, it has to be noted in this connection that the width of the support casing of the electronics module corresponds with only about half of the height, and particularly amounts to between 5 and 9 mm, e.g., to 7.5 mm. This permits individual tools and the electronics module to be manipulated and actuated particularly ergonomically for the hand, and in a comfortable manner. Furthermore, utilizing the connection pins for connecting the individual side walls and, if necessary, partitions that are used in any case, to begin with, as a bearing axle for supporting the tools and the electronics module, simplifies the entire assembly of the pocket tool to a substantial extent.

Another embodiment is beneficial as well in that it now permits uncoupling of the electronics module from the second coupling component with low exertion of force, on the one hand, and coupling of the electronics module with the second coupling component, on the other, with the first coupling component automatically locking on a support surface of the second coupling component. The spring force is optimized in a preferred manner in the detent arm with respect to expenditure of force.

In a further embodiment, the design is also advantageous in that any unintended swiveling of the electronics module from its storage position while the pocket tool is being transported, is excluded to the greatest possible extent, and the spring force in the detent arm of the electronics module and thus the expenditure of force for coupling and uncoupling the electronics module with 1 from the housing can be kept low, because when the electronics module is in its stored position, a constant retaining force is adjusted between the coupling components supporting one another via the clamping arm arrested on the bearing axle. Said retaining force is only released again when the bearing axle is lifted from the depression on the clamping arm and moved across the detent nose up to the circular arc-shaped raceway, whose radius corresponds with the radius of swivel of the support casing of the electronics module.

However, further embodiments offer advantages as well in that it is possible by means of the closing cap to store the interface of the electronics module as the pocket tool is being transported, and thus protect it from harmful environmental influences such as, e.g. dirt, splash water and the like, as well as from mechanical stress. In a preferred embodiment, the closing cap can be axially adjusted between its opening and closing positions in the direction of the longitudinal axis of the pocket tool, and can be swiveled versus the housing. The swivel-mounted closing cap has a second end wall element with a support surface for a first wall of the interface on the narrow side, via which the electronics module, with an adjusting movement of the closing cap from the closing into the opening position, is simultaneously swiveled from its storage position into a defined removal position. Additional handle elements on the electronics module can be omitted in this way. Any unintentional outward swiveling of the closing cap and thus of the electronics module is reliably prevented via a locking device between the closing cap and the housing. In another embodiment, the closing cap may be formed by a part area of the housing of the pocket tool, which reduces the number of individual construction components and provides the pocket tool with a compact construction.

According to still other embodiments, the memory may be formed by a flash memory card or an RFID, which store data and/or programs in a nonvolatile manner. Such nonvolatile memories with re-recordable memory surfaces are based on semiconductor technology and operate in a reliable manner.

In one embodiment, data exchange takes place between the memory or control circuit and a data processing system such as computers, or peripherals such as printers and scanners and the like, with the help of contacts. For this purpose, use is made of the standardized USB plug connectors or FireWire™ plug connectors, or corresponding connector bushes known from the prior art, which are characterized by their high data transmission rates.

Finally, however, the utilization of an interface via which data or signals are transmitted wirelessly, is advantageous as well. Such standardized interfaces are known in the market as Bluetooth™ and WLAN (Wireless Local Area Network) interfaces.

The functional scope of a pocket tool can be significantly expanded by means of a control circuit that is arranged in the pocket tool and designed for processing digitized media information, and that the pocket tool can be applied by the user with greater versatility. In addition to the mechanical functionality that is customarily available, such a pocket tool provides the user with an electronic functionality for the mobile processing of digital information as well, whereby the pocket tool is portable and has a small structural size. In particular, a device for processing media data is provided that permits the reproduction and/or recording of audio, video and picture information without depending on the location. This offers the user the benefit of not having to rely on any independent devices for digital information processing and mechanical activities. Beneficial possibilities for using the pocket tool as defined by the invention are available, for example in its application as a media reproduction device or multi-media player, particularly an audio and/or video player; as a dictating device; a digital camera; as a navigation device supported by map material stored in the memory, etc.

The pocket tool may be structured in a beneficial manner in the form of a modular tool via functional components, whereby individual functional components, which may be releasable from the housing of the pocket tool, if need be, are forming components comprising functional units and circuits of the control circuit and/or at least one peripheral. This permits later refitting of individual functional components for extending or changing the scope of medial and control functions of the pocket tool, and to exchange individual functional components as required.

The utilization of a peripheral formed by a storage element was found to be beneficial because the storage element can be integrated in the electronics module, and the latter with the storage element can always be carried along and used in the housing of the pocket tool without being dependent on any location. The utilization of a peripheral formed by the data interface is advantageous in that it permits linking stationary and, in comparison to the pocket tool, large-sized mass storage units with the control circuit.

Owing to the features of still other embodiments, a computer structure as known in the prior art can be usefully employed. Such a computer structure can be accommodated in the pocket tool in a structurally compact manner, and its control functions are very flexible and can be determined adaptively by control means.

An advantageous embodiment of the control means is, whereby the control logic formed as software permits free programming of the control instruction sequences of the control circuit, and the software can be extended or exchanged or updated in a simple manner for changing the control instruction sequences, whereby the structure of the hardware in the pocket tool can remain the same without any change.

Another design variation is found to be beneficial as well. According to said variation, the control circuit can be accommodated in an additional storage element with a nonvolatile read-only memory, in particular a ROM memory, or a fixed storage space can be assigned to the control circuit in the first storage element. In such a fixed storage area, the control logic is stored in the form of a preferably unchangeable initial program loader, particularly a so-called firmware. Thus the control functions of the control circuit are not directly changeable by the user, and any unauthorized manipulation of the control logic and thus the risk of functional errors in the control logic can be prevented by the user. However, the storage element can be erased and a new control logic can be stored in the form of a software update by the manufacturer or by service personnel, or by the user personally via additional measures, for example by calling in an external computer-operated update software communicatively connected with the control circuit.

The invention also contemplates embodiments where, it is possible to advantageously save storage space in the storage element, and media information with an overall much longer playback or running time can be stored in an uncompressed form. Furthermore, formats established in the prior art such as, for example MP3 and WMA can be played or processed for the first time with a pocket tool via the control circuit.

By means of a signal and/or data bus, it is possible to transmit energy and/or data between peripherals arranged in different positions or in different functional components of the pocket tool and/or the control circuit.

Owing to the other features of the invention, it is possible in spite of the modular construction to exchange signals between individual, structurally independent functional components in their operating or receiving positions in the housing of the pocket tool.

An advantageous design variation of the bus interface for connecting different electronics modules or functional components via contact elements is also disclosed.

Another design variation is useful in that the riveted pins normally present in the pocket tool for forming the housing can be employed at the same time as elements for transmitting signals, so that separate lines for the signal and/or data bus need not to be available, or only so to a limited extent.

Additional features of the invention are beneficial in that it is possible to output via an input and/or output interface the signals computed and transmitted by the control circuit, to terminal equipment such as audio and/or video output devices as known from the prior art, particularly to external loudspeakers or video screens or image projectors, in a form that can be understood and processed by such known devices. Furthermore, if necessary, analog input signals can be transmitted from a recording device, for example a microphone or a video or picture camera to the control circuit via the input and/or output interface as well, whereby the analog input signal is converted into a digital data record and stored in the memory. Signal amplifiers, and analog-to-digital converters (ADC's) and digital-to-analog converters (DAC's) etc., can be additionally assigned to the input and/or Output interface.

Furthermore, other features are beneficial in that it is possible by means of sound and/or visual input and/or output devices to output media information via the pocket tool in a form that is comprehensible to the user in terms of content, without necessarily requiring external equipment accessories. For example, it is possible via the input and/or output interface integrated in the pocket tool to output and record media information in the graphical and/or acoustic form, and to store such information in the storage element in the digital form. Moreover, the input and/or output device may serve as a status indicator for various parameters or processing modes of the control circuit.

Advantageous design variations of the pocket tool are also disclosed in that with said variations, the control circuit can be parameterized in a manner simple for the user. Particularly intuitive and user-friendly control is feasible via a user surface allotted to the controlling device, and by means of an electronic position detection system, particularly a touch screen, it is possible to provide a particularly compact structure of the control circuit, display and controlling device with just a few individual components.

Other useful exemplified embodiments of the pocket tool are disclosed that provide for simple controllability and adjustability of the functions of the control circuit.

Another useful embodiment of a peripheral, whereby it is advantageous particularly on account of an energy supply device formed by a self-sufficient energy storage according to claim 112, is that the pocket tool is not restricted in its mobility, and that the control circuit can be operated substantially without being dependent on any location. Particularly chemoelectrical energy storage means and especially rechargeable batteries can be employed in this connection, for example such as lithium or lithium-polymer accumulators, or one-way batteries.

Furthermore, a disclosed design variation is beneficial in that owing to the energy supply system provided in the pocket tool in the form of electrical conductors, the pocket tool either does not require its own energy storage means because electrical energy is supplied to the control circuit and to peripherals via the electrical conductors, or the energy storage means arranged in the pocket tool is rechargeable via the electrical conductors.

The invention further contemplates and discloses advantageous design variations for arranging the control circuit and at least one peripheral.

A further, independent solution to the problem as defined by the invention relates to another disclosed functional component. The benefit ensuing therefrom lies mainly in the fact that the first coupling component of the functional component serving for the connection to the other coupling component, comprises at the same time the bearing component, forming a pivot-mounted bearing site. The capability of the functional component of swiveling out of a receiving area in the housing of the pocket tool is therefore provided via the first coupling component, and the functional component can be released from the housing of the pocket tool in its swiveled-out condition.

BRIEF DESCRIPTION OF THE DRAWINGS

The invention is explained in greater detail in the following with the help of the exemplified embodiments shown in the drawings, in which:

FIG. 8 is a perspective view of the pocket knife with the electronics module set to a removal position.

FIG. 12 is another side view and simplified representation of a coupling component of the coupling device of the pivot bearing.

FIG. 12a is a side view of a part section of the pocket knife with another design of a pivot bearing, and of a part section of the electronics module, the latter being inseparable from the housing.

FIG. 13 is a perspective view of the pocket knife, with the electronics module completely detached and separated from its casing.

FIG. 14 is a side view of the pocket knife and electronics module shown in a preliminary position prior to coupling it with the second coupling component of the housing.

FIG. 15 is a side view of a part section of the pocket knife and electronics module in a preliminary position prior to uncoupling it from the second coupling component of the housing.

FIG. 18 is a longitudinal section and highly simplified representation of another possible design variation of a locking device disposed between the support casing of the electronics module and the housing of the tool card.

DETAILED DESCRIPTION OF PREFERRED EMBODIMENTS

Figure 1:
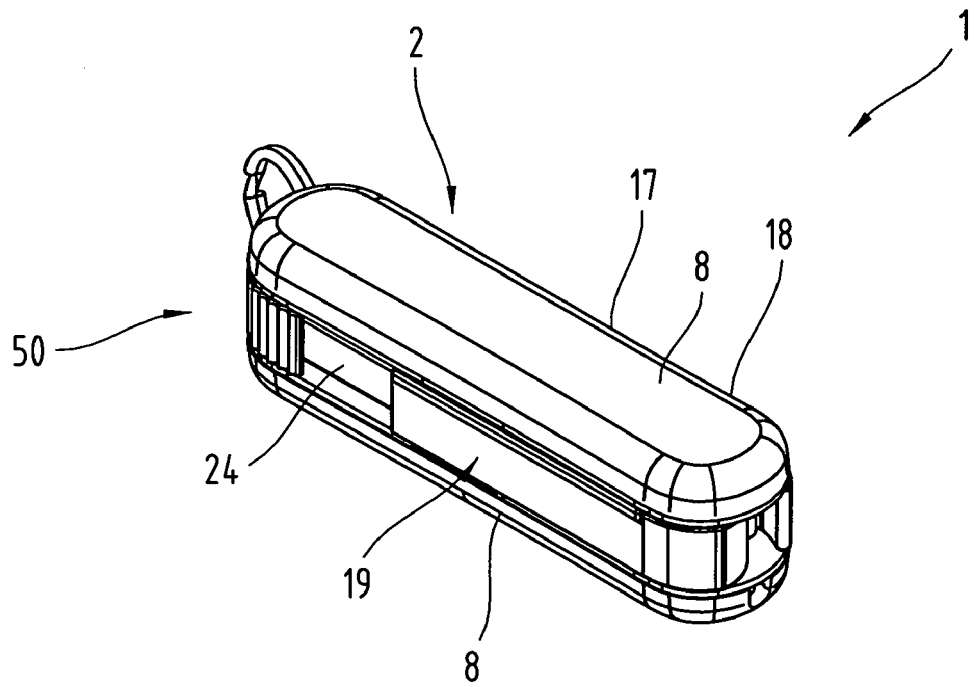
FIGS. 1 and 2 show perspective views of the pocket knife as defined by the invention, with an electronics module set to the storage position within the receiving area.
Figure 2:
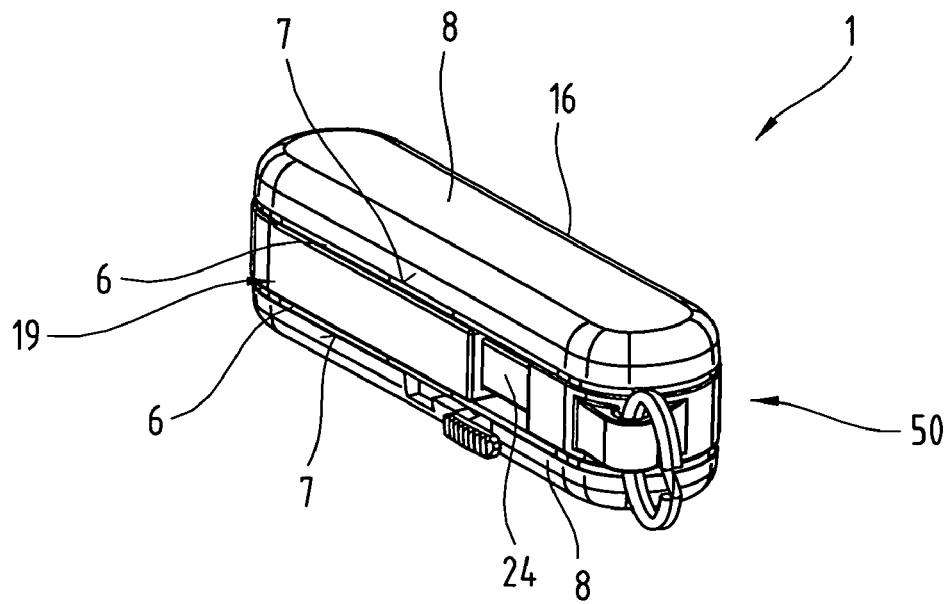
Figure 3:
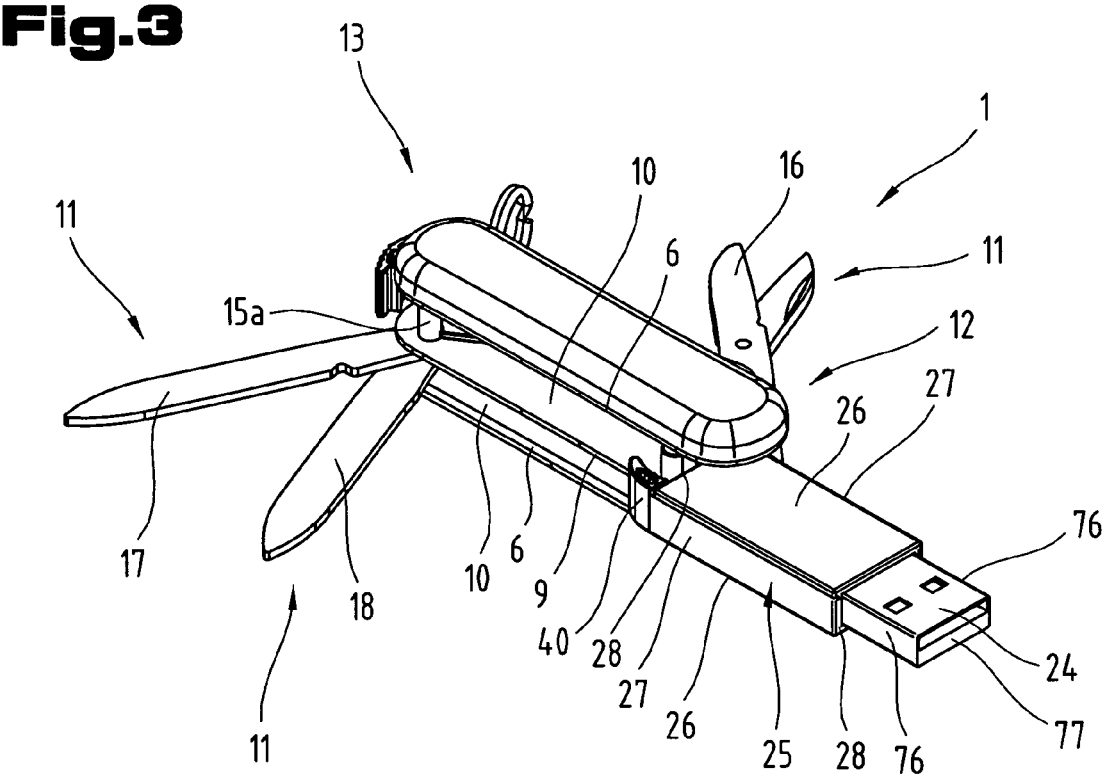
FIGS. 3 and 4 show perspective views of the pocket knife according to FIGS. 1 and 2, with the tools swiveled out, and the electronics module swiveled out into the position in which it is used.
Figure 4:
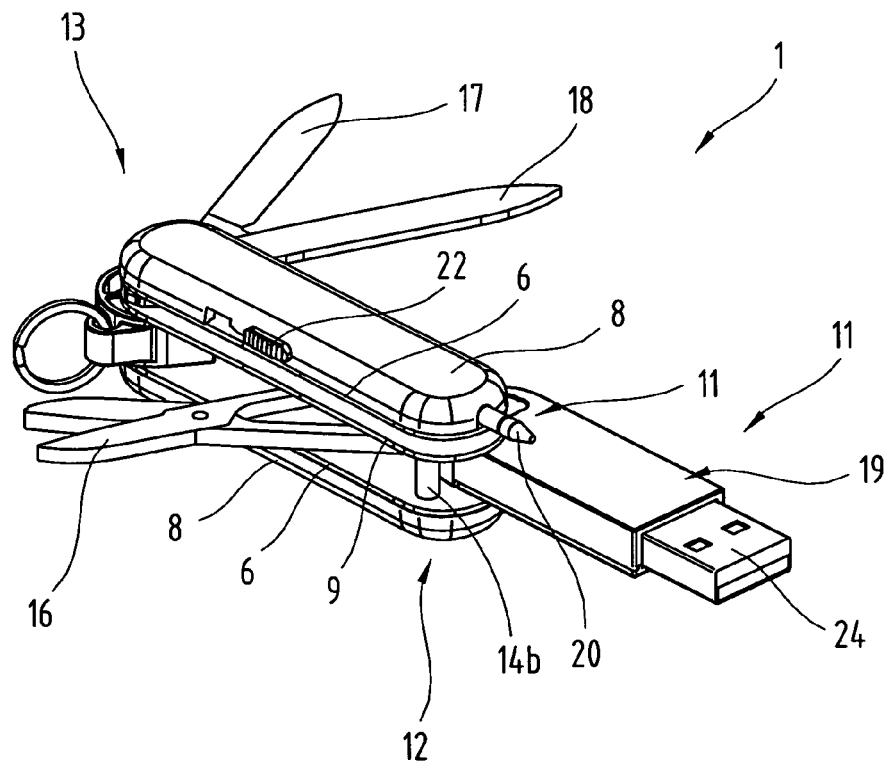
Figure 5:
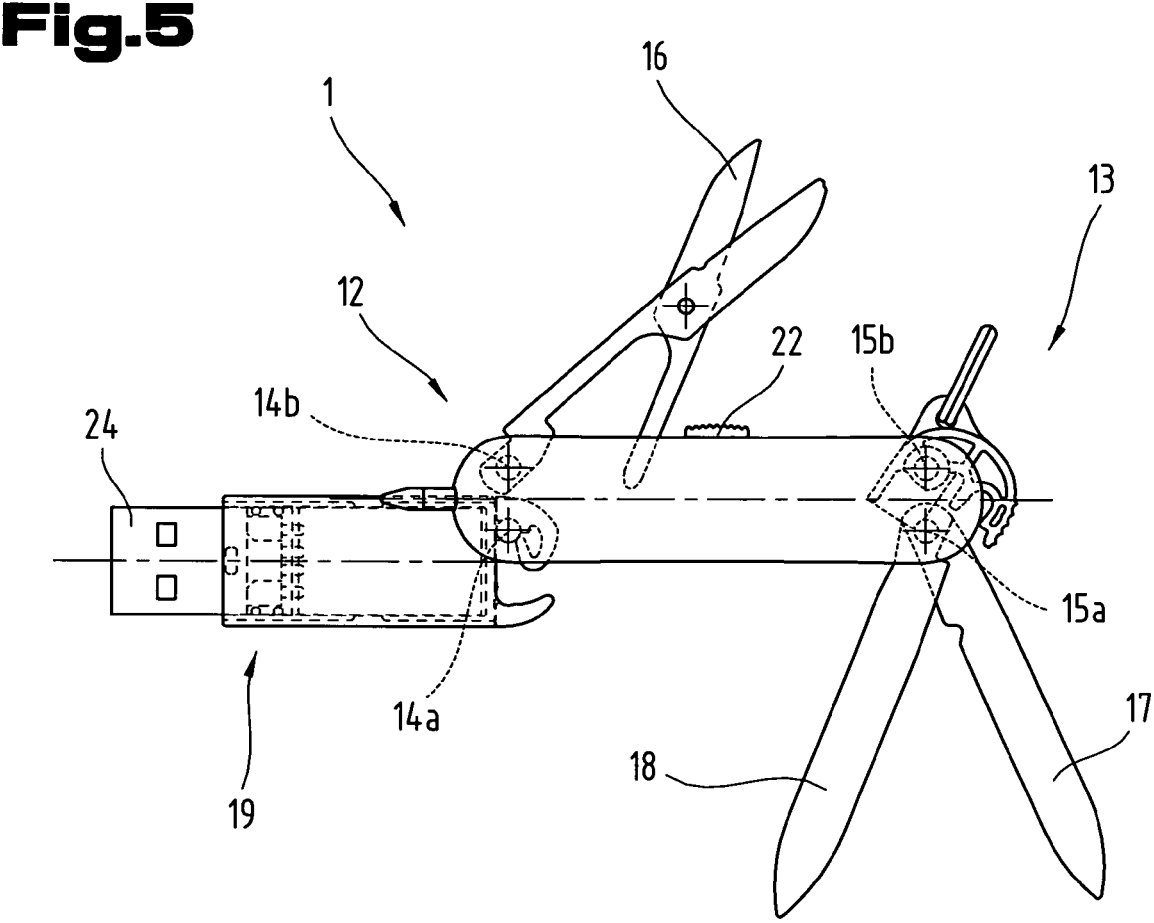
FIG. 5 is a side view of the pocket knife according to FIG. 4.

It is noted herewith by way of introduction that in the different embodiments described herein, identical components are provided with identical reference numerals and identical component drawings, and that the disclosure contained throughout the specification can be applied in the same sense to identical reference numerals and identical component drawings. Furthermore, data relating to positions such as, e.g. top, bottom, laterally etc. relate to the directly described and shown figures, and have to be applied in the same sense to the new position where a position has changed. Moreover, individual features or combinations of features in the different exemplified embodiments shown and described herein may per se represent independent inventive solutions, and solutions as defined by the invention.

The jointly described FIGS. 1 to 15 show a first design variation of the pocket tool as defined by the invention. According to said variation, the pocket tool is formed by a pocket knife 1, which comprises a housing 2 having a width 3 and a length 4 measured at a right angle in relation to the width. The housing 2 comprises a receiving body 5 made of, for example metal, with the two outer side walls 6, so-called outer plates disposed opposing one another, and the two cover plates 8, which are secured on the outer side surfaces 7 of the side walls 6 that are facing away from each other. Said cover plates 8 are formed, for example by an opaque or a transparent plastic. In the exemplified embodiment shown, a partition 9 or a so-called center plate is arranged between the two outer side walls 6, and the two receiving areas 10 for receiving the different functional components 11, are formed between the two side walls 6 and the partitions 9, said receiving areas being arranged partly separated from one another by the center plate. The two receiving areas are each at least partly limited by the side walls and partitions 6 and 9, respectively, and are arranged at least partly separated from each other in several planes at least partly disposed next to each other; and are extending parallel to the side surfaces 7 of the outer side wall 6, as well as between the front-side end areas 12 and 13 of the pocket knife 1, said end areas opposing one another. As shown in FIG. 1, each receiving area 10 is preferably accommodating two functional components 11.

It is not shown in greater detail that the cover plates 8 comprise bores arranged recessed on the inner sides of said plates facing the side surfaces 7. Said bores are provided for receiving the front ends of the bearing axles 14a to 15b, particularly riveted pins, the latter being shown, e.g. in FIGS. 6 and 9. The cover plates 8 are secured on the outer side walls 6 of the pocket knife 1 by press fit. The bearing axles 14a to 15b to be inserted in the bores connect the individual side wall and partition 6 and 9, respectively, as well as the functional components 11 arranged between said walls with each other. The functional components 11 are pivot-mounted on the bearing axles 14a to 15b. Preferably, two bearing axles 14a,b and 15a,b arranged one on top of the other and extending perpendicular to the side surfaces 7, are arranged in each of the end areas 12, 13 of the pocket knife. Center axes of the bearing axles 14a,b and 15a,b arranged one on top of the other, are extending congruently and aligned with each other. The housing 2 comprises the bearing axles 14a, 14b, 15a, 15b.

One of said functional components 11 is designed in the form of an electronics module 19, which is pivot-mounted on the first bearing axle 14a arranged in the face-side, first end area 12, and between the outer side wall and partition 6 and 9, respectively, in the first receiving area 10. Said electronics module 19 is adapted for being pivoted preferably by up to 180°, from a storage position located within the receiving area 10 or receiving body 5, which is shown, e.g. in FIGS. 1 and 2, into the working position outside of the receiving area 10 or receiving body 5 shown, e.g. in FIGS. 3 and 4.

Another functional component 11 is designed in the form of a pair of scissors 16, which is pivot-mounted on the second bearing axle 14b arranged in the face-side first end area 12, and arranged between the outer side wall and partition 6 and 9, respectively, in the first receiving area 10 as well. Said functional component 11, which is spring-loaded by a spring not shown, is adapted to pivot preferably by 90° or 180°, from a storage position within the receiving area 10 or receiving body 5 shown, e.g. in FIGS. 1 and 2, into its working position outside of the receiving area 10 or receiving body 5 shown, e.g. in FIGS. 3 and 4.

Two additional functional components 11 are formed by a knife 17 and a file 18, which both are pivot-mounted on the first bearing axle 15a arranged in the face-side second end area 13, and arranged between the outer side wall and partition 6 and 9, respectively, in the second receiving area 10. Said functional components 11 are each adapted to pivot under the load of springs not shown, from their storage positions in the receiving body 5 within the receiving area shown, for example in FIGS. 1 and 2, into their working positions shown in FIGS. 3 and 4 located outside of the receiving area 10 or receiving body 5, preferably swiveling by 90° or 180°. Thus the pair of scissors 16, the knife 17 and the file 18 are forming tools.

A closing cap still to be described in the following further below is pivot-mounted on the second bearing axle 15b arranged in the second end area 13 on the front side. Said closing cap is arranged between the outer side wall and partition 6 and 9, respectively, in the first receiving area 10 as well.

The individual figures show, furthermore, that a functional component 11 in the form of a writing pen 20 is arranged in at least one of the two cover plates 8. Said pen can be actuated by a slide 21 (see FIG. 7) guided in a longitudinal slot (not shown in detail) in the cover plate 8. Thus the writing pen 20 serves as a utensil as well. Said longitudinal slot is formed on an inner side of the cover plate 8 facing the side wall 6. Said slide can be locked in its end position, in which it is retracted as shown, e.g. in FIG. 1, and also in an end position in which it is extended, as shown, e.g. in FIG. 4. For its actuation, the slide has an actuation element 22 protruding from the contour of the cover plate 8. Such a writing pen and the constructional design of the longitudinal slot, as well as the cover plate 8 and the actuation element 22 are already known from the prior art, and are disclosed in detail in WO 99/07247 A of this Applicant. On the one hand, the functional component 11 or utensil may be formed also by a toothpick, pincers, or a cleaning needle and the like. Furthermore, at least one of the cover plates 8 may have a number of longitudinal slots for receiving a number of utensils, if so required.

According to a solution as defined by the invention, which is represented in FIGS. 1 to 18 with the help of different exemplified embodiments, the functional component 11 is designed in the form of an electronics module 19 with an interface 14 and a memory, said module having an oblong support casing 25. The latter comprises the two side walls 26 on the broad sides, which are opposing each other with a spacing between one another, and on the narrow sides the side walls 27 and 28 extending at right angles to said walls 26.

Figure 10:
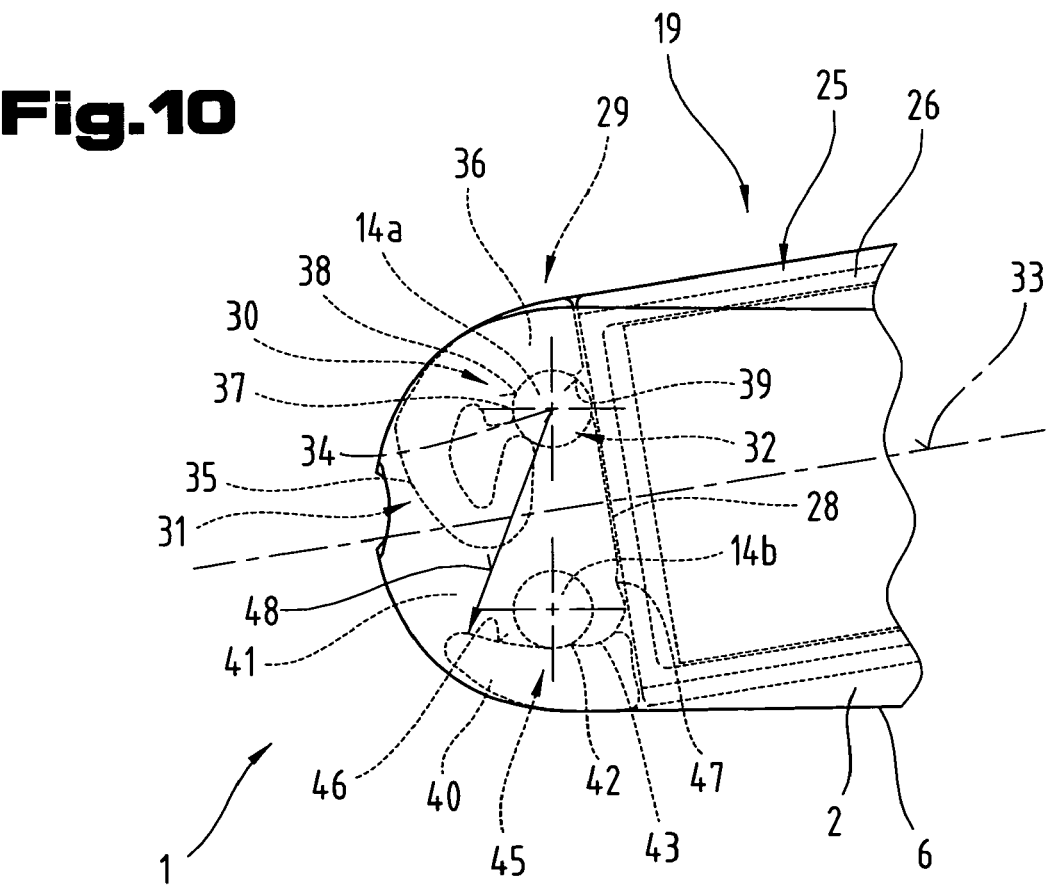
FIG. 10 shows an enlargement of a cutout of the pocket knife according to FIG. 9, with the pivot-mount arranged between the support casing of the electronics module and the housing of the pocket knife, as well as its coupling device with a first design of the coupling components.

The enlarged representation in FIG. 10 shows that a pivot bearing 29 is arranged between the electronics module 19 or support casing 25, and the housing 2 of the pocket knife 1, said bearing in turn being equipped with a coupling device 30. The latter comprises the two coupling components 31, 32, which can be engaged with and released from one another, whereby the first coupling component 31 is arranged in the face-side first narrow-side wall 28, and the second coupling component 32 in arranged in or articulated on the housing 2 of the pocket knife 1. In the present embodiment, the second coupling component 32 is formed by the first bearing axle 14a in the first end area 12 of the pocket knife 1. The first coupling component 31, which is arranged in the face-side first end area of the support casing 25, is forming an axle 34 arranged offset in relation to the longitudinal center axis 33 of the support casing 25, said axle 34 extending perpendicular to the side surfaces 7 of the side walls 6, or perpendicular to the broad-side walls 26. With its first end area, the support casing 25 of the electronics module 19 is accordingly pivot-mounted on the first bearing axle 14a, and comprises the first coupling component 31.

The first coupling component 31 comprises a partly spring-elastic detent arm 35 freely cantilevered on the face-side, first narrow-side wall 28, and a bearing component 36, the latter being rigid versus the detent arm 35. Said detent arm 35 is formed by a detent or snap element and consists of two arm sections bordering one on the another. The first arm section is directly adjoining the bearing component 36, and the second arm section, which is connected with the first arm section, is extending in the direction opposing the one of the latter. The free end of the detent arm 35, particularly of the second arm section, is pressed against or supported on the bearing surface 39 of the second coupling component 32 with a spring or holding force preset by the resiliency of the detent arm 35, whereas the bearing component 36 is guided on the second coupling component 32 via an approximately half shell-shaped or split bearing cup 37 arranged coaxially with the second coupling component 32. The bearing component 36 or split bearing cup 37 is forming a bearing surface 38 adapted to complement at least by sections a bearing surface 39 of the second coupling component 32. The detent arm 35 is usefully tapered in the direction of its free end. With the detent arm 35 engaged on the bearing surface 39 of the second coupling component 32, the electronics module 19 is capable of reliably pivoting versus the housing 2.

FIG. 10 shows, furthermore, that the support casing 25 of the electronics module 19 is additionally equipped with a slightly flexural clamping arm 40 freely cantilevered on the face-side, first narrow-side wall 28. Said clamping arm is arranged offset versus the longitudinal center axis 33 of the support casing 25 in the direction of the side opposing the first coupling component 31. A receiving slot 41 for receiving the second bearing axle 14b is formed between the first coupling component 31 and the clamping arm 40, said receiving slot extending in about the direction of the longitudinal expanse of the support casing 25. On its side facing the first coupling component 31, the clamping arm 40 is provided with a detent nose 42 protruding into the receiving slot 41, said detent nose and the bearing axle 14b arranged in the housing 2 jointly forming a releasable, if need be, locking device 45. The detent nose 42 is extending parallel to the axle 34. Starting from the face-side end area of the support casing 25 and extending in the direction of its longitudinal expanse, the clamping arm 40 has a depression 43 and a circular arc-shaped raceway 46, each facing the bearing axle 14b. The depression 43 and the raceway 46 are separated from each other via the detent nose 42, whereby the latter protrudes into the raceway 46. The radius 48 of the raceway 46 corresponds with the radius of swivel of the support casing 25. With the electronics module 19 in its storage position, the bearing axle 14b is locked on the depression 43, whereas starting with a predefined removal position of the electronics module 19, in which the latter adequately protrudes from the outer contour for it to be seized by hand, the bearing axle 14b is resting against the raceway 46 and capable of sliding on the latter. In the course of the further swiveling movement, the clamping arm 40 slides with its raceway 46 on the bearing axle 14b. In order to prevent the bearing axle 14b from being levered out of the depression 43, the support casing 25 is additionally equipped with a holding nose 47 projecting from the first narrow-side wall 28. Arranging the clamping arm 40 offers the advantage that as the pocket knife 1 is being transported, or when the electronics module 19 is completely pivoted into its storage position, and thus when the longitudinal center axis 33 of the support casing 25 and the longitudinal axis of the pocket tool are extending congruently, the first coupling component 31 is pressed against the second coupling component 32 with a constantly maintained holding force, so that any unintentional uncoupling of the electronics module 19 from the housing 2 is avoided. The electronics module 19 therefore can be reliably transported jointly with the pocket knife 1 in the form of one structural unit. The clamping arm 40 thus serves also as a means securing the electronics module 19 against losing it.

Figure 11:
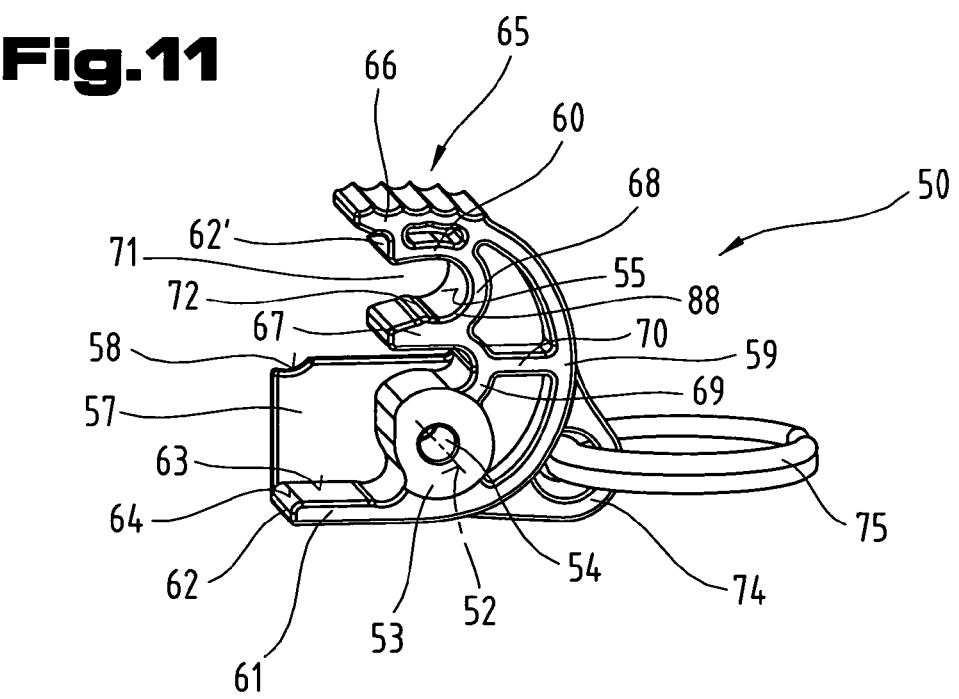
FIG. 11 is a perspective view of the closing cap for protecting the interface of the electronics module, the latter being fully pivoted into its storage position.
Figure 9:
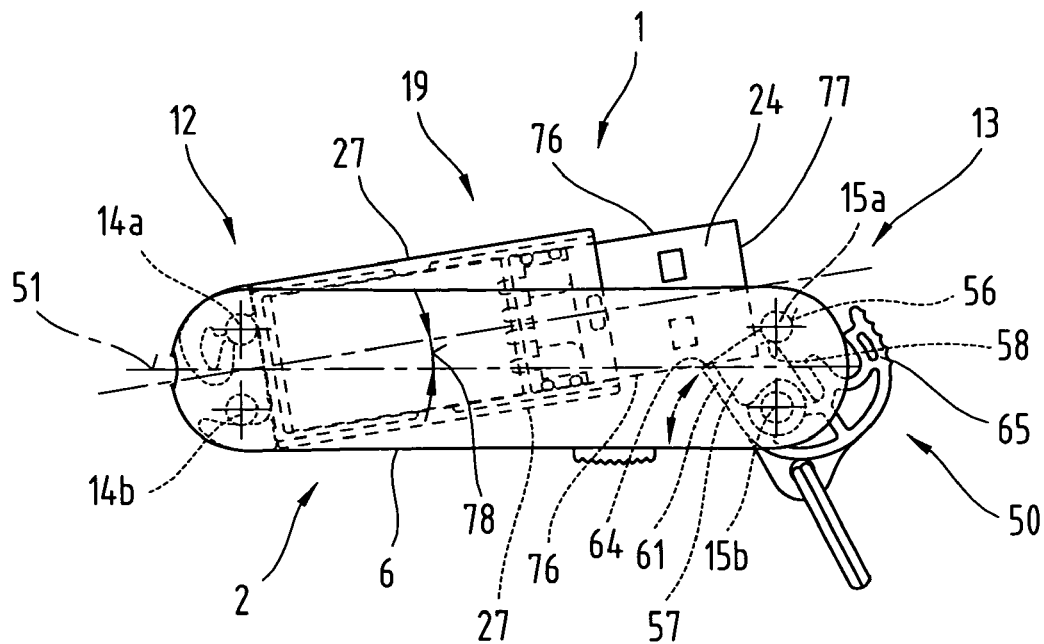
FIG. 9 is a side view of the pocket knife according to FIG. 8.

Furthermore, the housing 2 comprises a closing cap 50 pivot-mounted on the second bearing axle 15b arranged in the second end area 13 of the pocket tool, which is shown in detail particularly in FIGS. 9 and 11. The second end area 13 is disposed opposing the first end area 12. The closing cap 50 is arranged between the side wall and partition 6 and 9, respectively, which are disposed parallel to one another, and is adjustable between a closing position shown in FIGS. 1 and 6, and an opening position shown by way of example in FIGS. 3 and 9, as well as in relation to the housing 2, and particularly adapted for pivoting. The electronics module 19 or support casing 25 and the closing cap 50 are arranged within the same first receiving area 10 in the storage and closing positions.

Figure 6:
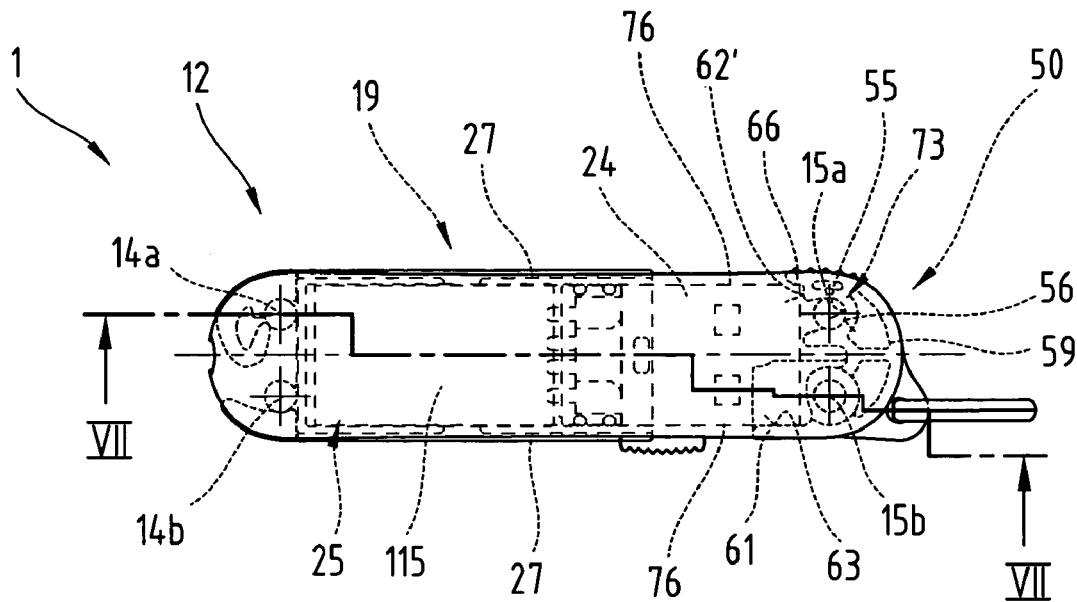
FIG. 6 is a side view of the pocket knife according to FIG. 2.

As shown in FIG. 11 by an enlarged representation, the closing cap 50 is approximately sickle-shaped and comprises an axle 52 arranged offset relative to the longitudinal axis 51 of the housing 2, and extending perpendicular to the side surfaces 7 or broad-side walls 26. Furthermore, the closing cap 50 is equipped with an about boss-like pivot bearing area 53 with a bearing bore 54 extending perpendicular to the side surfaces 7 or broad-side walls 26, said bore being penetrated by the bearing axle 15b; as well as with a first stop surface 55 on an inner side facing the receiving area 10. In its closing position as shown in FIG. 6, the closing cap 50 is supported via the first stop surface 55 on a stop surface 56 formed in the housing 2, particularly by the bearing axle 15a.

A wall element 57 rising laterally perpendicular to the axle 52 of the bearing bore 54, is formed at one end of the bearing bore 54, forming another stop surface 58, whereby the closing cap 50, in its opening position as shown in FIG. 9, is supported with the other stop surface 58 on the stop surface 56 in the housing 2, particularly with the bearing axle 15a.

An outer wall 59 of the sickle-like closing cap 50 is shaped in a part section in the form of a circular arc, and has, at the end of said cap, a first end-wall section 60 connected with said closing cap, and at the second end of said cap a second, plane end-wall section 61 connected with said cap.

The pivot bearing area 53 adjoins the second end of the wall 59. The end-wall section 61 is an extension of the wall 59 and has a freely cantilevered front edge 62, which is offset vis-à-vis the pivot bearing area 53 in the direction leading to the first receiving area 10, as well as a plane support surface 63 extending between the face edge 62 and the pivot bearing area 53. Said plane support surface 63 is facing the first receiving area 10 and serves as a support for the interface 24 of the electronics module 19, the latter being completely pivoted into its storage position. The interface 24 is described in detail further below. FIG. 11 shows that that in the area of the face edge 62, the second end wall section 61 is provided with a curved support surface 64, which serves for supporting the interface 24 of the electronics module 19 when the latter is in its removal position, in which it is completely pivoted outwards.

The wall section 57 described above projects vertically from the stop surface 63 and extends across part of the spacing between the first and second end-wall sections 60 and 61, respectively. The first end-wall section 60 is equipped with an actuation element 65, which, with its free face end 66, projects beyond a freely cantilevered face edge 62' formed by the first end-wall section 60. The face end 66 jutting out from the face edge 62', and the second end-wall section 61, as well as the wall 59 are jointly forming a protective cap which, when the electronics module 19 is not in use, or when it is shifted into its receiving position, protects the interface 24 from dirt and mechanical stress. The top side of the actuation element 60 is grooved.

A detent arm 67 freely jutting out from the wall 59 on the inner side, is arranged between the first end-wall section 60 and the boss-like pivot bearing area 53. On the one hand, said detent arm 67 is connected with the first end-wall section 60 via a curved first connection wall 68, and on the other hand with the pivot bearing area 53 via a curved second connection wall 69, forming one piece therewith. A plane third connection wall 70 is extending between the second connection wall 69 and the wall 59. A guide slot 71 limited by guiding surfaces facing one another, is formed between the face end 66 or first end- wall section 60, and the detent arm 67. Said guide slot has an open front side in the direction of the first receiving area 10, and is limited by the first connection wall 68 on the front side disposed opposite said open front side. The connection wall 68 is forming the stop surface 55.

The closing cap 50 forms a detent nose 72 protruding into the guide slot 71, said detent nose being molded onto the detent arm 67. Jointly with the bearing axle 15a arranged in the housing 2, said detent nose 72 (see FIG. 6) is forming a locking device 73 that can be released, if need be. Thus the locking device 73 is arranged between the closing cap 50 and the housing 2. The detent nose 72 extends transversely to the direction of adjustment of the closing cap 50, particularly parallel to the axle 52. The closing cap 50 therefore can be locked in its closing position via the locking device 73. Furthermore, FIG. 11 shows that the closing cap 50 is provided with a flange 74 on an outer side facing away from the first receiving area 10, said flange forming a through-extending bore. A key ring 75 penetrates the through-extending bore and is movably connected with the flange 74.

The cooperation between the second functional component 11 forming the electronics module 19, and the closing cap 50 is now explained in greater detail in the following with the help of FIGS. 8 and 9. When the electronics module 19 has to be moved, particularly swiveled from its storage position within the first receiving area 10, into its working position outside of the first receiving area 10, the closing cap 50 is first adjusted, i.e. it is pivoted from its closing position shown in FIG. 6, into its opening position shown in FIG. 9, by applying actuating force to the actuation element 65.

With the electronics module 19 in its pivoted-in storage position, the interface 24, which is sensitive to dirt and mechanical stress, is arranged between the two side walls 6, the first end-wall element 60 or front end 66, and the second end-wall element 61, as well as the curved wall 59 extending between said walls. In this connection, the interface 24 is overlapped over part of its length by the first end-wall element 60 or front end 66, and the second end wall element 61 on its two narrow side walls 76, the latter extending parallel to the narrow-side walls 27 of the support casing 25, and opposing one another. At its open front side 77, where the electrical contacts are arranged, the interface 24 is preferably completely covered by the wall 59. In this way, the electrical contacts, which are arranged within the region of the open front side 77 of the interface 24, are reliably prevented from getting soiled and exposed to mechanical stress as the pocket tool is being transported. This is not shown in any greater detail. The side wall and partition 6 and 9, respectively, which are disposed adjacent to the electronics module 19 when the latter is in its swiveled-in storage position, prevent dirt from penetrating the interface 24, and mechanical stress from acting on the support casing 25.

With the electronics module 19 in its storage position, the interface 24 partly rests with the first narrow-side wall 76 on the support surface 63 (see FIG. 6).

The electronics module 19 is swiveled out from its storage position into the removal position shown in FIG. 9 simultaneously with the outward pivot motion of the closing cap 50. When in said removal position, the electronics module 19 can then be seized and completely swiveled outwards into is working position located outside of the receiving area 10. After the electronics module 19 has been pivoted into the position from where it can be removed, it can be swiveled out into the working position as required. When in the position for its removal, the electronics module 19 protrudes from the receiving area 10 only to the extent allowing it to be seized by the user in a simple manner, and with only minor application of force.

As briefly mentioned already above, in the position for removal, the interface 24 rests with its narrow-side wall 76 on the support surface 64 of the second end-wall element 61; the wall element 57 rising up is supported via its stop surface 58 on the stop surface 56 formed by the longitudinal axle 15a; and the longitudinal center axis 33 of the electronics module 19 and the longitudinal axle 51 of the pocket tool jointly enclose an angle 78, which is dimensioned in such a manner that the electronics module 19 and/or the interface 24 protrude at least partly from the outer contour of the pocket tool. The angle 78 can be defined as required by dimensioning the wall element 57 formed with the stop surface 58, and the wall element 61 with the support surface 64 accordingly.

The electronics module 19 and the closing cap 50 are coupled for moving jointly: when the closing cap 50 is moved from its closing into its opening position, the electronics module 19 is simultaneously moved from its storage position into the removal position. In this process, the bearing axle 15a locked in a depression 88 delimited by the detent nose 72 and the stop surface 55, is lifted from the depression 88, and lifted out beyond the detent nose 72 and up to the free end of the detent arm 67, on the one hand. On the other hand, the bearing axle 14b is lifted out of the depression 43 delimited by the detent nose 42 and the holding detent 47, and adjusted beyond the detent element 42 in the direction of the free end of the clamping arm 40 up to the raceway 46. As the respective bearing axles 14b and 15a are sliding across the detents 42 and 72, respectively, said detents 42 and 72 as such are elastically deformed, and/or the clamping and detent arms 40 and 67, respectively, are slightly deflected in the direction perpendicular to the longitudinal expanse of the detent elements 42 and 72. After jumping across the detent elements 42 and 72, the clamping and detent arms 40 and 67, respectively, which are flexible, if necessary, are automatically reset to their original positions. As the electronics module 19 is being swiveled outwards further from the removal position in the direction of its working position, said raceway 46 causes the electronics module 19 to swivel outwards smoothly vis-à-vis the housing 2.

Contrary to the above, when the electronics module 19 has to be moved, particularly pivoted from its working position outside of the receiving area 10, into the position where it is stored within the receiving area 10, it is first pivoted inwards until it is in its removal position, where the interface 24 will again rest with its first narrow-side wall 76 on the support surface 64 of the closing cap 50, the latter having been pivoted outwards into its opening position, whereupon force of pressure applied to the freely accessible narrow-side wall 27 of the support casing 25 and/or the actuation element 65 of the closing cap 50, the clamping and detent arms 40 and 67, respectively, with the detent noses 42 and 72, respectively, are adjusted in the same sense vis-à-vis the bearing axles 14b and 15a, respectively, and the latter are automatically locked in the depressions 43 and 88, respectively. In this process, the closing cap 50 is pivoted from its opening into its closing position, where the stop surface 55 of the closing cap is supported on the stop surface 56 in the housing 2.

FIG. 12 is a side view of a part section of the pocket tool as defined by the invention. The pivot bearing 29 is arranged between the support casing 25 of the second functional component 11 forming the electronics module 19, and the housing 2. According to the present embodiment, the pivot bearing 29 comprises a pivot bearing area 79 with a bearing bore 80 arranged in said area, and is pivot-mounted on the bearing axle 14a of the housing 2 via said bore. The pivot bearing 29 comprises the coupling device 30, which comprises the coupling components 31, 32, which are engageable with and disengeable from one another. The first coupling component 31 is formed on the support casing 25, and the second coupling component 32 is formed by an adapter 81 pivot-mounted on the bearing axle 14a, the latter being immovably arranged in the housing 2. Said adapter 81 and the support casing 25 each have at least one plug or detent or snap element forming the first and second coupling components 31 and 32. The plug or detent or snap elements are adapted to complement and engage one another. The second functional component 11 is connected with the adapter 81 via a plug or detent or snap connection between said component 11 and said adapter 81, such connection forming the coupling device 30, and is releasable from said adapter as required.

In the embodiment shown, the coupling device 30 is formed by a plug or friction grip connection. The first coupling component 31, which is arranged on the support casing 25 in the face-side first end-area facing the adapter 81, is usefully formed by part sections of the broad- and/or narrow-side walls 26 and 27, respectively, opposing one another; and the second coupling component 32 formed by the adapter 81, is formed by a plug socket 82. The friction grip between the broad- and/or narrow-side walls 26 and 27, respectively, of the support casing 25, and the inner walls of the plug socket 82 of the adapter 81, can be adjusted as required.

In another embodiment not shown in detail, the coupling device 30 may be formed by a detent system, in which the second functional component 11 or electronics module 19 forming the latter, and the support casing 25 are secured in a detachable manner in or on the adapter 81 by a detent element, for example by means of a spring-loaded ball.

The pivot bearing 29 comprises the clamping arm 40 already described above, and the slot 41 for receiving the detent nose 42 protruding from the bearing axle 14b into said slot formed for the bearing axle 14b between the pivot bearing area 79 and the clamping arm 40. The detent nose 42 and the bearing axle 14b jointly form the locking device 45. Via said locking device 45, which is releasable as required, the second functional component 1 can be locked at least in its storage position within the first receiving area 10 not shown in the present figure.

Now, it is possible via said coupling device 30 to use the second functional component 11 or the electronics module 19 forming the latter, completely separated from and independently of the pocket knife 1, as it is shown in FIG. 13. In such a case, the working position of the second functional component 11 is understood to be the position in which the electronics module 19 is used completely separated from the pocket knife 1, and is connected, for example via the interface 24 to a data processing system such as a computer or laptop, for exchanging data between the latter and the electronics module 19.

It is explained in greater detail in the following with the help of FIGS. 14 and 15 how the electronics module 19 is coupled with and uncoupled from the housing 2, particularly the bearing axle 14a.

For coupling the electronics module 19 to the bearing axle 14a having the housing 2, the following steps are carried out: the closing cap 50 is first set to its opening position, and the electronics module 19 is then directly positioned with the receiving slot 4 above the bearing axle 14a and about perpendicular to the longitudinal axis 5 of the pocket knife 1. Thereafter, the electronics module 19 is moved in the vertical direction relative to the longitudinal axis 51 towards the bearing axle 14a of the pocket knife 1 as indicated by arrow 83; the bearing axle 14a in inserted in the receiving slot 41, and subsequently displaced as indicated by arrow 84 parallel to the longitudinal axis 51 in the direction of the closing cap 50 until the detent arm 35 of the first coupling component 31 is locked on the bearing surface 39 of the second coupling component 32, so that the first and second coupling components 31 and 32, respectively, are flexibly connected with each other. After it has been locked, the electronics module 19 is pivoted into the storage position within the first receiving area 10 not shown in the present figure.

The electronics module 19 is uncoupled from the bearing axle 14a having the housing 2 by carrying out the coupling steps shown in FIG. 15 in the reserve order: the electronics module 19 is first swiveled into a position where the clamping arm 40 and the bearing axle 14b are disengaged from each other. An uncoupling force is subsequently applied to the electronics module 19, said force acting on the latter according to arrow 85 about perpendicular to the longitudinal center axis 33 of the electronics module 19 against the retaining force of the detent arm 35, so that the second section of said detent arm 35 is deflected radially outwards with respect to the bearing axle 14a as indicated by the dash-lined arrow, and released from the bearing surface 39 of the bearing axle 14a, whereupon the movement of the electronics module 19 causes the first coupling component 31 to be uncoupled from the second coupling component 32 or the bearing axle 14a forming the latter, between the longitudinal axis 51 of the pocket tool and an angular direction relative to the longitudinal center axis 33 of the electronics module 19 as indicated by arrow 86.

Figure 16:
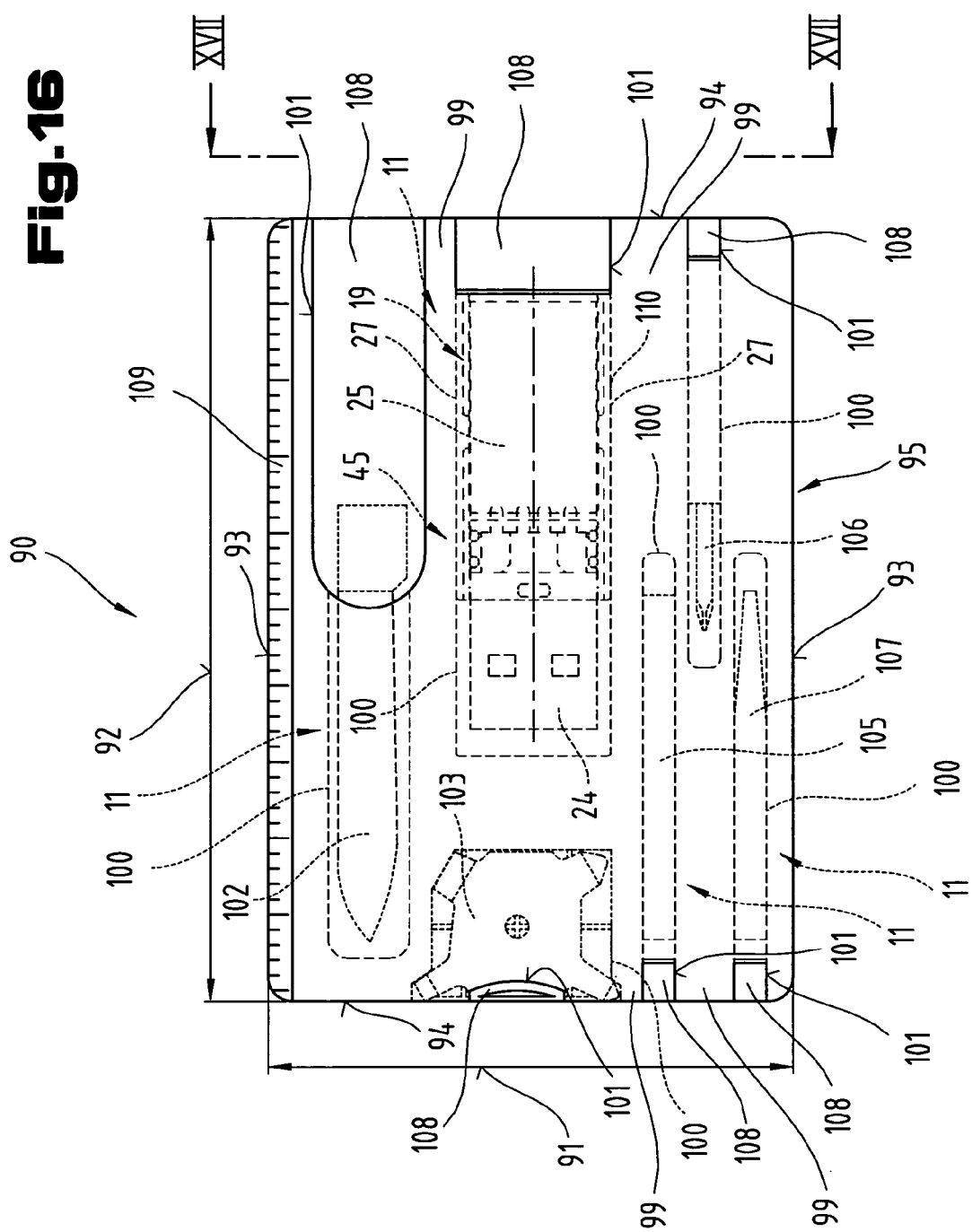
FIG. 16 is a top view of a plate-like tool card shown by a highly simplified representation.
Figure 17:
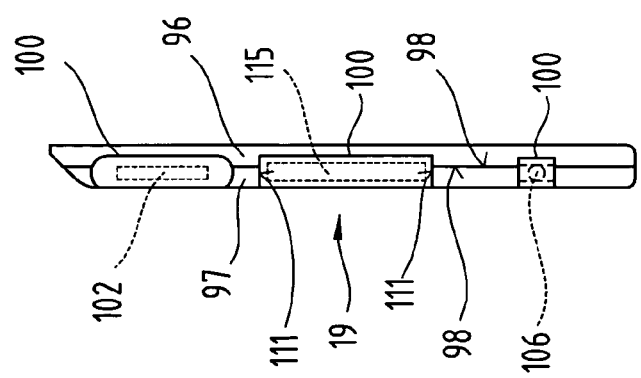
FIG. 17 is a highly simplified view of the tool card according to FIG. 16 according to lines XVII—XVII.

The jointly described FIGS. 16 and 17 show different views of another design variation of the pocket tool as defined by the invention. The present pocket tool is formed by a plate-like tool card 90 made of metal and/or plastic and has a rectangular outline with a width 91 and a length 92 measured at right angles to the width. Two longitudinal side surfaces 93 are spaced apart by the width 91 and extend at right angles relative to the cross-side surfaces 94 spaced apart by the length 92. The plate-like tool card 90 comprises a casing 95 substantially having the contour of a credit or calling card.

The casing 95 of the tool card 90 has a base plate 96 and a cover plate 97 extending substantially parallel to the base plate. Said two plates are inseparably joined with each other and have the side surfaces 98 facing one another. In a plane extending parallel to the base and cover plates 96 and 97, respectively, the casing 95 has a plurality of the receiving areas 100, which are at least by sections separated from each other by the partitions 99. Said receiving areas receive a multitude of the functional components 11, which are accessible from the outside via the receiving openings 101. The receiving areas 100 are least partly arranged within the casing 95 between the base and cover plates 96 and 97, respectively. It is obvious under this aspect that with the present design variation, the functional components 11 are completely separated from the casing 95 in their respective working positions, and can be used independently of the casing.

The removable functional components 11 are formed, for example by a knife 102, a so-called multifunctional tool 103, an electronics module 19, pincers 105, a Phillips screwdriver 106 for Phillips head screws, and a toothpick 107. Each of said functional components is movable between a storage position within the receiving area 100, and a working position located outside of the storage position 100, and has a handle 108 which, with the functional component 11 in its storage position, projects into the receiving opening 101.

The two figures show that one of the longitudinal-side surfaces 93 is connected via a slanted surface with an external surface of the cover plate 97. Said slanted surface is extending at right angles relative to said longitudinal-side surface 93 and is inclined in the direction of the external surface, starting from said side-surface 93, and is provided with a rule for measuring length.

According to the present design variation, several partitions 99, which are disposed parallel to one another and at least partly separated from one another, are molded onto the inner side surfaces of the base and cover plates 96, 97, respectively, distributed over said side surfaces facing each other. Said partitions are not shown in detail in the present figures. The partitions 99 project from the base plate 96 in the direction of the cover plate 97, and vice versa from the cover plate 97 in the direction of the base plate 96 vertically relative to the inner side surfaces, and each extend approximately over the entire inside height between the inner side surfaces, so that with the cover plate 97 mounted on the base plate 96, the partitions 99 are disposed next to each other, and, via a connecting element, are connected with their face edges facing the inner side surfaces of the base and cover plates 96, 97, respectively, with said inner side surfaces.

In another embodiment, it would be conceivable also to mold several partitions 99 onto the inner side surfaces of the base and cover plates 96 and 97, respectively, such partitions being disposed parallel to each other distributed over said side surfaces and being at least partly separated from one another. Such partitions 99 project from the base plate 96 in the direction of the cover plate 97 and vice versa from the cover plate 97 in the direction of the base plate 96 perpendicular to the inner side surfaces, and are each extending only partly over the entire inside height between the inner side surfaces facing each other, and running toward each other when the cover plate 97 is mounted on the base plate 96. The partitions 99 opposing each other are inseparably connected with each other via a connecting element on their face edges facing each other. In this way, a partition 99 extending over the entire inside height between the base and cover plates 96, 97 is formed in each case.

On the other hand, it is possible also to mold several partitions 99 extending parallel to each other only onto one of the side surfaces of the base and cover plates 96, 97, such partitions being at least partly separated from each other and extending over the entire inside height between the base and cover plates 96, 97. Via their face edges, the partitions 99 on the base and cover plate 96, 97 are inseparably connected with the inner-side surface of the opposite base or cover plate 96, 97, via a connecting element. The partitions 99 rise vertically relative to the inner side surface.

The connecting element may be formed by a seam of adhesive and/or welding seam and/or a detent or snap connection. The partitions 99 keep the base and cover plates 96 and 97, respectively, spaced from each other, and delimit the receiving areas 100 at least by sections.

In other embodiment, the casing 95 is comprised of the base and cover plates 96, 97, respectively, and an intermediate plate arranged between the base and cover plates. The base or cover plate 96, 97 has the receiving openings 101 for the handles 108 of the functional components 11, whereas the receiving areas 100 are exclusively arranged in the intermediate plate and formed there by recesses. The recesses are delimited by the partitions 99 and have contours complementing the functional components 11 at least in part.

According to a solution as defined by the invention, a releasable locking device and a longitudinal guide 110 are arranged between the support casing 25 of the second functional component 11 or the electronics module 19 forming the latter. The longitudinal guide 110 extends over part of the length of the tool card 90 and preferably parallel to the longitudinal axis of the tool card 90. The longitudinal guide 110 for the electronics module 19 or support casing 25 is formed by two partitions 99 disposed next to each other and the inner side surfaces of the housing 95 facing the broad-side surfaces 26. Said guide is at least partially delimited by the latter, and has the two guide surfaces 111 parallel opposing each other, said surfaces being formed by the partitions 99. The guide surfaces 111 extend parallel to the narrow-side walls 27 of the support casing 25, and parallel to the longitudinal axis of the tool card 90.

The locking device 45 is arranged between the support casing 25 of the electronics module 19 and the casing 95, and, in the present exemplified embodiment, is formed by a friction grip connection between the support casing 25 of the electronics module 19 and the housing 95. For such friction grip connection, the support casing 25 has at least one friction grip element preferably formed by a part area of at least one of the broad-side and/or narrow-side surfaces 26 and 27, respectively. Likewise, the housing 95 has at least one friction grip element as well, the latter being preferably formed by a part area of the longitudinal guide 110, particularly at least one, preferably both guide surfaces 11 and, if need be, the inner surfaces facing at least one, preferably both two broad-side surfaces 26.

The friction grip elements may each extend over part length of the longitudinal guide 110 and/or the support casing 25, and may be formed in the front and/or end areas viewed in the direction in which the electronics module 19 is inserted, or in the first and/or second end areas, or over the entire length of the longitudinal guide 110 and/or support casing 25. As already explained above, the friction grip connection between the inserted second functional component 10 or electronics module 19, and the longitudinal guide 111 may be influenced in a targeted manner by preparing the surfaces accordingly. For example, adequate retaining or holding force can be obtained through increased surface roughness of the surface parts of the broad-side and/or narrow-side walls 26, 27 of the support casing 25 and the longitudinal guide 110 to be engaged, particularly the guide surfaces 111 and, if need be, the inner surfaces of the base and cover plates 96, 97 facing each other, or by changing the dimensions of the surface parts to be engaged in terms of space, so that the second functional component 11 inserted in its storage position, is reliably locked via friction grip in the transport position of the tool card 90, and said functional component 11 can be prevented from accidentally sliding out of the receiving area 100. Preferably, the locking device 45 has only part of the length of the longitudinal guide 110.

Another embodiment of the locking device is shown in FIG. 18. In its storage position, in which it is inserted in the receiving area 100, the second functional component 11 or electronics module 19 is detachably arrested by positive lock between the support casing 25 of the electronics module 19 and the linear guide 110 or receiving area 100, particularly between the partitions 99 and/or the base or cover plate 96, 97. Now, provision may be made that the housing 95, particularly the base and/or cover plates 96, 97 have a slightly elastically yielding detent nose on at least one of their inner side faces 112 in the receiving area 100, and the second functional component or the support casing 25 has a locking deepening facing the detent nose 113 and complementing the latter, so that in its storage position, the electronics module 19 is locked between the detent nose 113 and the locking deepening 114. The detent nose 113 and the locking deepening 114 extend transversely to the longitudinal expanse of the longitudinal guide 110. The locking device 45 formed by the detent nose 113 and the locking depression 114, naturally may be arranged also between the narrow-side walls 27 of the support casing 25 and the parallel partitions 90 disposed adjacent to said walls. The detent nose 113 projects into the receiving area 100.

The functional components 11, particularly the electronics module 9, can be releasably locked in their inserted storage positions via positive lock and/or friction grip between the respective functional component 11, particularly between the support casing 25 and/or handle 108, and the longitudinal guide 110 or the receiving area 100, particularly the partitions 99 and/or inner-side surfaces of the base and cover plates 96 and 97, respectively.

Figure 7:
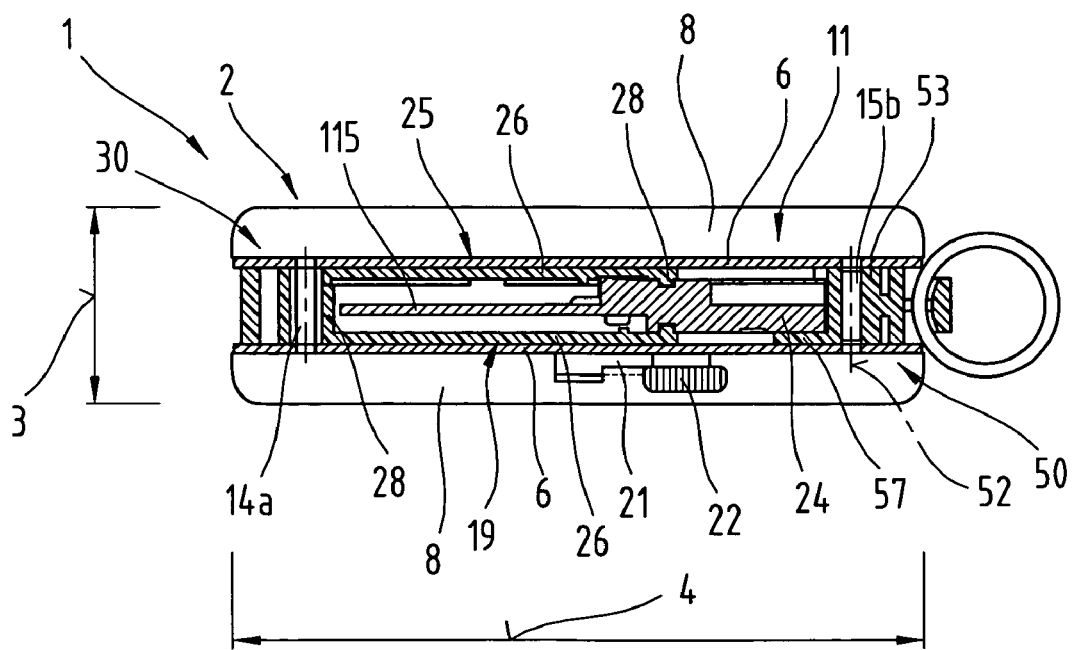
FIG. 7 is a section along lines VII—VII in FIG. 6.

The second functional component 11 described above, or the electronics module 9 forming said component, comprise a memory card 115 or the memory as shown, for example in FIGS. 6 and 7, and the interface 24. The memory card 115 has a recordable and readable nonvolatile, in particular semiconductor (SC) memory (flash ROM), or is formed by a radio frequency identification device (RFID). The RFID is a chip on which data are stored passively and therefore does not transmit signals, but receives radio waves from transmitters or reading devices and will thereupon release its information. The RFID is supplied with the energy required for transmitting data by the radio signals it is receiving. The memory card 115 naturally may be formed by a smart or chip card, a flash card, or a so-called multimedia card as well.

For reading electrical signals or electronic data into the memory, and for reading out such electrical signals or electronic data, the electronics module 19 is equipped with at least one interface 24. In a preferred embodiment, the interface 24 is formed by a USB connector or connector bush, or a universal serial bus or a FireWire™ connector or connector bush (IEEE 1394). Such interfaces are characterized by their high rates of data transmission. Said interface 24 is equipped with electrical contacts for the data exchange between the memory and a data processing system such as a computer, or peripherals such as printers, scanners etc.

Such a nonvolatile memory is characterized by its positive property that the memory contents are not lost if the supply voltage is switched off, and that they are recordable up to 1 million times. Programs such as control and processing programs and/or data of any desired type such as text data, data relating to image or speech information, audio and video files such as, for example MP3, can be stored in a nonvolatile manner on such a memory.

As opposed to the interface 24 shown in the embodiments, where data or signals are transmitted via contacts, data can be written in or read out also in a wireless manner, particularly inductively, capacitively, optically, or purely telemetrically, and therefore via a radio frequency. For this purpose, the interface 24 has a transmitter and/or receiver, and is formed, for example by an infrared interface or radio signal interface. Such standardized interfaces 24 are known from the prior art, and the expert is familiar with them under the trade name WLAN interface or Bluetooth™. The interface 24 is quasi formed as a moving arm disk capable of maintaining the memory contents without requiring external supply voltage.

So as to prevent any unauthorized use of the data stored in the memory in case the electronics module is lost after it has been uncoupled and removed from the pocket tool, it is possible also to provide the support casing 25 of the electronics module 19 with a sensor for biometric access control. Such a sensor can be formed, for example by a fingerprint sensor. Furthermore, the electronics module 19 may also comprise an electronic circuit in the form of a microchip comprising the readable and recordable nonvolatile memory.

Finally, it is noted here, furthermore, that in another embodiment as shown in FIG. 12*a*, the pivot bearing has no coupling device 30, and the electronics module 19 is exclusively pivot-mounted on the bearing axle 14*a* and inseparable from the housing 2. The electronics module 19 is adapted for pivoting from the storage position within the receiving area 10 or receiving body 5, into the working position outside of the receiving area 10 or receiving body 5, preferably by up to 180°, and is unexchangeably connected with the housing 2. The pivot bearing 29 is formed by the bearing axle 14*a* and the pivot bearing area 79 having the support casing 25 and a bearing bore 80. The same design could be conceivable also for the tool card 90.

Furthermore, if the pocket tool is designed as a pocket knife 1, it is possible that the electronics module 19 is incapable of pivoting, but movable between the storage and working positions in the direction parallel to the longitudinal axis 51, and in particular axially slideably supported in the housing 2. This is not shown in any detail. A longitudinal guide is provided for this purpose, which is formed by the two side surfaces 7 or a side surface and a partition 7, 9, respectively. The side surfaces facing each other form the guide surfaces, between which the support casing 25 is adjustably supported. The broad-side walls 26 are usefully supported on said guide surfaces after the electronics module 9 has been inserted in the storage position. With such a design, the closing cap 50 may be formed by the housing 2 and immovably connected with the latter, or it may be axially movable between the opening and closing positions in the direction of the longitudinal axis 51 toward the interface 24, or moved or set away from the latter. The closing cap 50, the latter being adjustable relative to the support casing 25 with of the electronics module 19 being inserted in its storage position, is axially displaceably supported in the housing 2 between the opening and closing positions.

The support casing 25 with the first coupling component 31 and the closing cap 50, is manufactured from plastic by injection molding.

A independent solution to the problem as defined by the invention pertains to a pocket tool, for example a pocket knife 1 or a plate-like tool card 90 with the housing 2; 95 and the receiving area 10; 100, and at least one functional component 11 movable from a receiving position within the receiving area 10; 100, into a working position outside of the receiving area 10; 100. Such a functional component may be formed by a tool, particularly the scissors 16 or knife 17; 102, or a utensil, particularly a toothpick 107; pincers 105; a cleaning needle; a writing pen 20 or the like, whereby the pocket tool has a electrical control circuit 120 and at least one peripheral 121 linked with said control circuit for electrical data transmission.

FIGS. 19 to 21 and 23 to 29 show possible design variation of the pocket tool comprising the control circuit 120 and at least one peripheral 121. A realizable structure of the control circuit 120 and the peripheral 121 is shown in FIG. 22 by a schematic block diagram.

The control circuit 120 is preferably formed by a computer structure comprising at least one processor unit 120a, an input/output system 120b, and a system bus 120c. The at least one peripheral 121 is formed by a digital storage element 122 or a data interface 123, whereby the pocket tool preferably comprises several peripherals 121, which may be formed particularly by the storage element 122 and/or the data interface 123 and/or an input/output interface 124, particularly an audio or video interface, and/or an input/output device 125 and/or an operating system 126 and/or an energy supply system 127. The peripherals 121 are electrically linked with the control circuit 120 via the input/output system 120b for signal transmission. Furthermore, a signal and/or data bus 128 may be linked with the input/output system 120b; the peripherals 121 and the control circuit 120 are communicatively connected with each other via said bus.

It is noted here that the storage element 122 may comprise a memory of the type described above in connection with FIGS. 1 to 18. Furthermore, the data interface 123 may be formed by the interface 124 described above. In another design variation, it is possible to permanently or inseparably integrate the storage element 122 in the housing 2; 95 of the pocket tool.

The data stored in the storage element 122 are accessible via the particularly digital data interface 123, whereby a one- or bidirectional data exchange may take place via the data interface 123, so that any desired data can be stored in the storage element 122 or read out from the latter irrespectively of their format or structure. For example, external data media, computer networks, data processing systems or the like can be connected via the data interface 123 with the control circuit 120 or storage element 122 for signal transmission, so that magnetic storage media with a large size in comparison to the pocket tool such as, e.g. fixed-disk or floppy disk storage media, or read-only memories such as CD-ROM's or DVD-ROM's can be used for data exchange with the control circuit 120 and the storage element 122, if installed. Such design variations are described in greater detail in the following.

A control means is assigned to the control circuit 120 that is designed for processing, particularly reproducing digitized media information stored in a memory, particularly in the storage element 122. Audio, picture or video information, for example, may be stored in the storage element in the form of digitized media information.

A pocket tool with a control circuit 120 designed in such a manner is advantageously extended with respect to the scope of its functions in that in addition to the computation of parameters based on analog measured values, and display of the latter in the numerical or alphanumerical form, it is possible also to process via special control means data previously transmitted to and stored in the storage element 122 in the digitized form via the data interface 123. The data may be stored in this connection in the storage element 122 as digitized audio information in the form of a data record, whereby the control circuit 120 converts such data record into a transmittable, particularly analog output signal that can be tapped via the input/output interface 123, or into a signal for controlling a sound input/output device 125 of the pocket tool, particularly a loudspeaker. Furthermore, the data may be stored in the storage element 122 in a data record as digitized picture or video information, which is converted by the control circuit 120 into an analog output signal or signal for controlling a visual input/output device 125 of the pocket tool, particularly a display. The information volume the control circuit 120 is capable of processing is, in this connection, substantially higher than it is in connection with exclusive processing of measured values, and other types of information can be processed as well, which means a wider application spectrum is available for the pocket tool, and the user benefits from the reproduction of all kinds of different information with enhanced reproduction quality. For example, on the visual input/output device, particularly an LCD display, it is feasible to output high-resolution picture and/or video information in color or black-and-white, and/or to output on the sound input/output device, particularly a sound generator, genuine sound reproduction. Moreover, a status display may be provided on the input/output device, whereby it is possible to display, for example the operating conditions of the control circuit 120 or peripherals 121, and/or to display, leaf through and select, when required, the data stored in the storage element 122.

The processor unit 120a of the control circuit 120 is preferably formed by a microprocessor and a main memory, particularly a dynamic random access memory (RAM). The control means of the control circuit 120 for converting digital media information stored in the storage element 122, into an applicable analog form, is preferably formed by a control logic stored or storable as software in the intermediate memory of the processor unit 120a. Furthermore, in terms of hardware, the control circuit 120 may comprise D-A and A-D converters for converting digital media information into analog signals, or vice versa. The control logic is preferably stored as a data record in a read-only memory that may be formed by a memory area in the first storage element 122, or the read-only memory is formed by an additional storage element 129, for example a programmable and erasable flash-ROM memory, or EEPROM (electrically erasable programmable read-only memory) memory. The control logic may be stored in the read-only memory as a preferably unchangeable initial loading program or bootstrap program, whereby the read-only memory can be erased and recorded again, if necessary, e.g. in order to update the control logic.

The digitized media information is stored in the storage element 122 preferably in the coded or compressed form, for example as an MP3 (MPEG-1 Layer 3—Movie Pictures Experts Group) or WMA (Windows Media Audio) data record. For processing the media information, the control logic or the control means of the control circuit 120 may comprise coding and/or decoding routines in order to convert the compressed or coded information in a transmittable output signal that can be understood by other peripherals 121. The media information basically can be stored in the storage element 122 in any desired data file format or data file structure, whereby the control means of the control circuit 120 is adapted to the format of the media information so as to be capable of processing the latter. The control logic of the control circuit 120 may be updateable, expandable or exchangeable, if need be, so that the control circuit 120 can be adapted to new or changing requirements of media information that is stored in the storage element 122 and to be retrieved from the latter.

The signal and/or data bus 128 may be provided for information or data exchange and/or for transmitting energy between various peripherals 121 and the control circuit 120. The electrical energy supplied by the energy supply system 127, in particular the operating voltage can be transmitted via the signal and/or data bus 128 to the control circuit 120 and the peripherals 121, if necessary. For this purpose, an self-sustained energy source may be allotted to the pocket tool, e.g. a rechargeable battery such as a lithium-ion accumulator, a button cell battery, or an AA- or AAA-sized battery as the energy supply system 127. Furthermore, it is noted herewith that the different peripherals 121 and each electronics module 19 may have its own energy supply system 127. Furthermore, the energy supply system 127 may be formed by electrical conductors of the signal and/or data bus 128, which may be connected via an energy supply interface to an energy source located externally of the pocket tool. The energy supply interface may be formed, for example by the data interface 123 which, in addition to data lines, may also comprise energy supply lines for tapping and transmitting operating voltage via the signal and/or data bus 128. Moreover, the energy supply interface may be provided with its own connection element.

In general, the second functional component 11 may be equipped with the particularly oblong support casing 25 for forming another design variation of the electronics module 19 with the control circuit 120 and/or the at least one peripheral 121. The functional component 11 or electronics module 19 is movably arranged for driving it from a storage position within the receiving area 10; 100, into a working position externally of the receiving area 10; 100 of the housing 2; 95. At least one locking device 45, which can be vented if required, and the longitudinal guide 110 or the pivot bearing 29 can be arranged in this connection between the support casing 25 of the second functional component 11, and the housing 2; 95. The structure of the functional component 11 is not addressed here in greater detail because it can be realized at least in part as already specified above in the description of FIGS. 1 to 18.

One or more peripherals 121 and/or the control circuit 120 may be arranged in the housing 2; 95 of the pocket tool, and such peripherals 121 and the control circuit 120 may be electrically linked in the electronics module 19 for signal transmission.

Basically, provision may be made for any desired number of functional components 11 in the receiving areas 10; 100 allocated to the housing 2; 95 of the pocket tool, whereby the number of such functional components 11 is determined by the structural size of the pocket tool and thus by the availability of volume for the receiving areas 10; 100. For example, one single peripheral 121 and the control circuit 120 may each form its electronics module 19, or several peripherals 121 and, if need be, the control circuit 120 may form an electronics module 19. In particular, at least the storage element 122, the data interface 123 and preferably the control circuit 120 and one of the input/output interfaces 124 jointly form a common electronics module 19.

Figure 19:
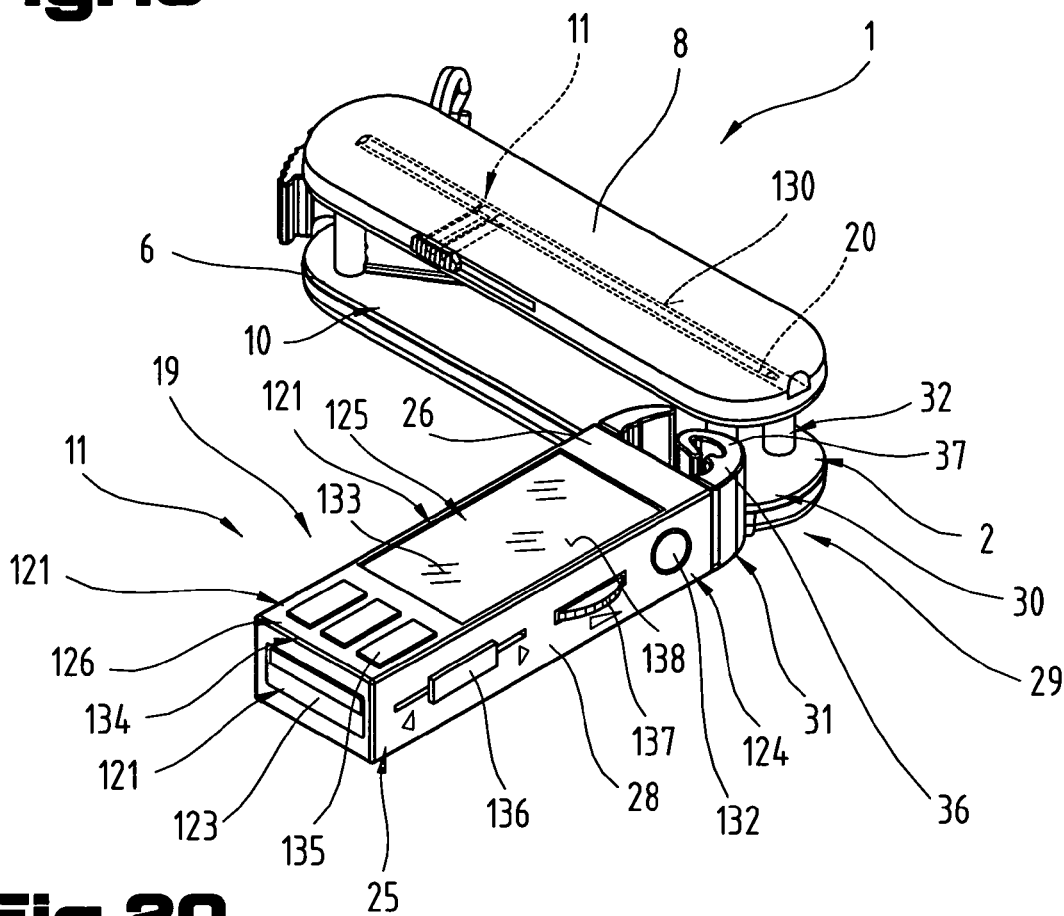
FIG. 19 is a perspective view of another design variation of the pocket knife with an electronics module comprising a control circuit and peripherals.

FIG. 19 shows a possible design variation of a pocket tool with the control circuit 120. The pocket tool is designed in the form of a pocket knife 1, where the first functional component 11 is arranged within the region of the cover plate 8. Said functional component 11 is formed here by a writing pen 20 of the type already specified above. Said writing pen is longitudinally displaceable in the direction indicated by the arrow shown. By actuating the slide 21, the first functional component 11 in the form of the writing pen 20 can be driven from the storage position shown within the storage area 10, into the working position, in which the writing pen 20 protrudes from the housing 2. In addition to the first functional component 11, one or more additional functional components 11 formed by tools or utensils of the type described above, can, of course, be arranged in the pocket knife 1 as well.

It is shown, furthermore, that a second functional component 11 is accommodated in the storage position in another receiving area 10 formed by a deepening on the narrow-side surface on the longitudinal side of the housing 2, whereby said functional component 11 comprises the support casing 25 having the broad-side wall 26 and the two narrow-side walls 27, 28, and the pivot bearing 29 with the coupling device 30.

In the exemplified embodiment shown in the present figure, the control circuit 120 and several peripherals 121 are jointly arranged in or on the support casing 25 of the second functional component 11 for forming the electronics module 9. The electronics module 19 is equipped there with the control circuit 120, the storage element 122, the data interface 123, the input/output interface 124, the input/output device 125, the operating device 126, as well as with the energy supply system 127. The electronics module 19 is consequently self-sustained and capable of operating independently for processing media information, and is in particular forming a discrete functional unit, whereby the electronics module 19 is mechanically coupled to the housing 2 via the coupling device 30. The electronics module 19 is preferably detachable from the housing 2, for which purpose the first coupling component 31 arranged on the support casing 25, is uncoupled from the coupling component 32 arranged on the housing 2 of the pocket knife 1, so that the electronics module 19 can be used, if required, separately from the housing 2 of the pocket knife, and can be serviced, for example by charging the energy supply system 127 on a battery charger, or for erasing information or storing new media information in the electronics module 19 on a computer system.

Figure 20:
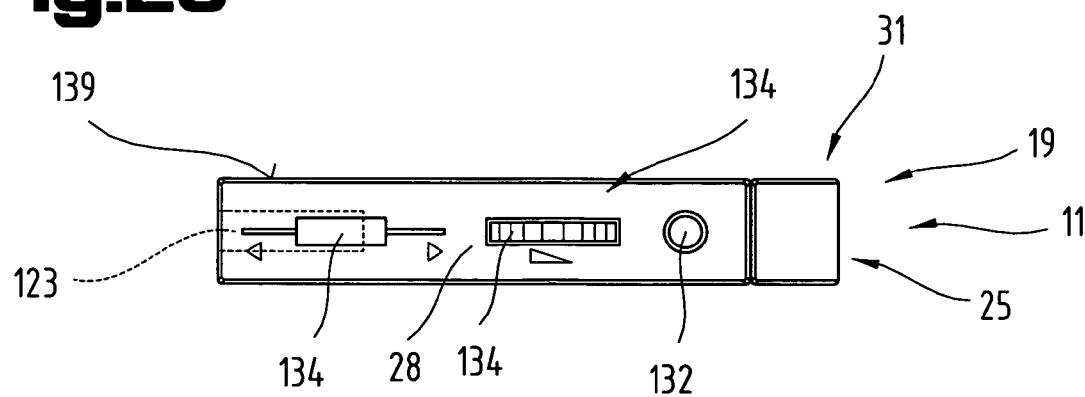
FIG. 20 is a side view of the electronics module according to FIG. 19.
Figure 21:
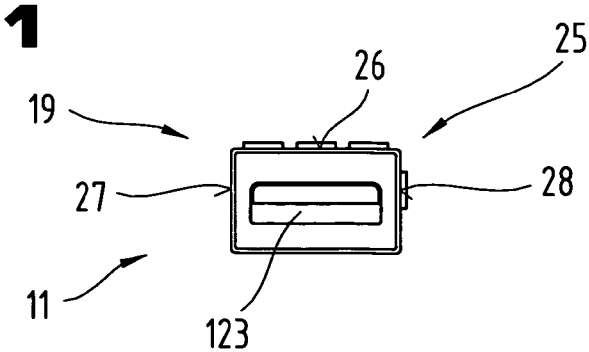
FIG. 21 is a front view of the electronics module according to FIG. 19.
Figure 22:
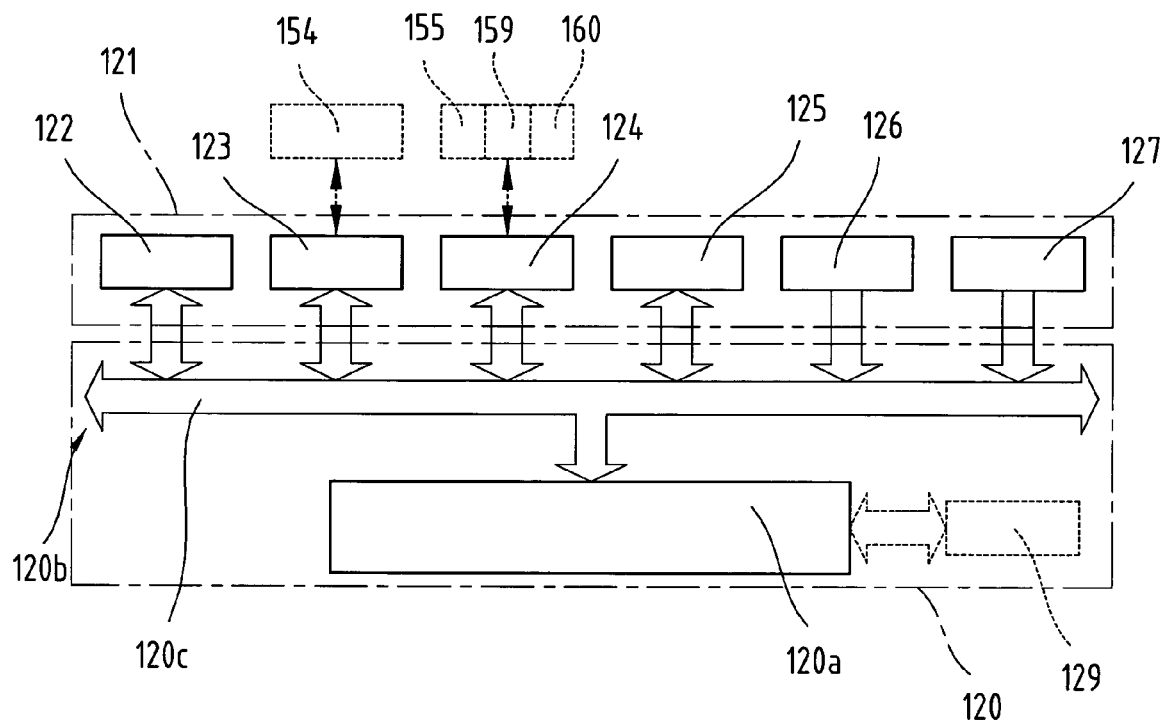
FIG. 22 shows a block diagram of the control circuit with different peripherals connected to said circuit.

FIGS. 20 and 21 show the electronics module 19 with the control circuit 120 in the position in which it is uncoupled from the pocket knife 1. The data interface 123 is arranged on the narrow-side wall 28 of the support casing 25. In the present exemplified embodiment, the data interface 123 is formed by a plug socket 131 comprising electrical contacts. The interface naturally may be formed also by a pin-like plug element as specified above in the description of the interface 24.

Furthermore, the input and/or output interface 124 is arranged on the narrow-side wall 28 for inputting or outputting electrical signals such as, for example audio and video signals. In the exemplified embodiment shown in the present figures, the input and/o output interface 124 is designed in the form of a jack 132 for connecting a sound generator such as, e.g. a loudspeaker, or an external audio amplifier/receiver, whereby a single- or multi-channel audio signal is output on the input and/or output interface 124. The jack 132 is designed, for example as a 2.5 mm or 3.5 mm jack. Furthermore, the input and/or output interface 124 may be formed by an optical or coaxial digital output. In particular, headphones, microphones, loudspeaker systems or the like can be connected to the jack 132.

In the present exemplified embodiment, the sound and/or visual input/output device 125 is arranged in the broad-side wall 26 of the support casing 25. The input and/or output device 125 is formed in the present case by a display 133 formed, for example by a liquid-crystal display (LCD) as known in the prior art. The display 133 is suitable for at least displaying numerical and alphanumerical information, whereby in a possible design variation, high-resolution representations such as, e.g. picture or video information can be visualized on the display 133 as well. A 1-bit black-and-white representation of information can be realized; however, information can be visualized on the display 133 also on gray levels with 8 bit, or in color with 16 bit, 24 bit or 32 bit color depth. Furthermore, one or more light sources with adjustable light intensity, if required, can be allocated to the display 133 for illuminating a zone of representation. In addition, the input and/or output device 125 can be designed in the form of light-emitting elements such as, e.g. light-emitting diodes (LED's) (not shown in detail).

Several input elements 134 of the operating system 126 are arranged on the support casing 25 of the electronics module 19. By way of example, the pressure-actuated key elements 135 are arranged on the broad-side wall 26, and a sliding key 136 and a particularly infinitely variable controller 137 are arranged on the narrow-side wall 27, whereby the input elements 134 each are electrically linked with the control circuit 120. The input elements 134 may be selected from the group of switching contacts or controllers such as, e.g. potentiometers as known in the prior art. Said input elements 134 are formed, for example for controlling the audio or video functionality of the control circuit 120 with an ON/OFF switch; a volume controller; a play/stop/title and data file selection switch; key locking and/or pause switch.

It is noted here that one of the peripherals 121 may be formed by an electrical position detection system, particularly a touch screen. In such a case, the display 133 and the input elements 134 are realized in a common physical unit, whereby the input elements 134 are visualized on the display 133 in a representation zone 138 within the area of the outer surface 139 of the support casing 25, and can be actuated by touching and applying pressure to the representation zone 138 of the display 133. For applying pressure to the representation zone 138 of the display 133, it is possible to use as a utensil, for example one of the tools or utensils arranged in the pocket tool such as, for example a toothpick, or an additional utensil intended for such purpose can be arranged in the housing 2 of the pocket tool, e.g. in the form of a non-staining operating pen for inputting commands on the display 133.

Furthermore, the storage element 122 and the control circuit 120 for processing the digitized media information stored in the storage element 122, are arranged in the support casing 25 of the electronics module 19. Operating parameters and operating conditions can be adjusted and controlled via the input elements 134 of the operating system 126. In a realizable design variation, an operating surface is visualized on the display 133 and/or by the light-emitting elements, e.g. a menu control, whereby the operating system 126 is equipped for navigating on the operating surface. The operating surface or menu control may comprise one or more selection panes, selection windows, register cards or the like displayable on the display 133 for fixing processing and reproduction parameters, objects and media data files to be reproduced, and display properties, whereby any menu controls known from the prior art can be employed.

Such a functional component 11 comprising the control circuit 120 and the peripherals 121 provides a compact, small-sized electronics module 19 permitting the reproduction of media such as, for example audio, pictorial and/or video information, which substantially expands the scope of application of the pocket tool for the user, so that such a pocket tool is capable of satisfying the latest requirements of modem information technology.

Figure 23:
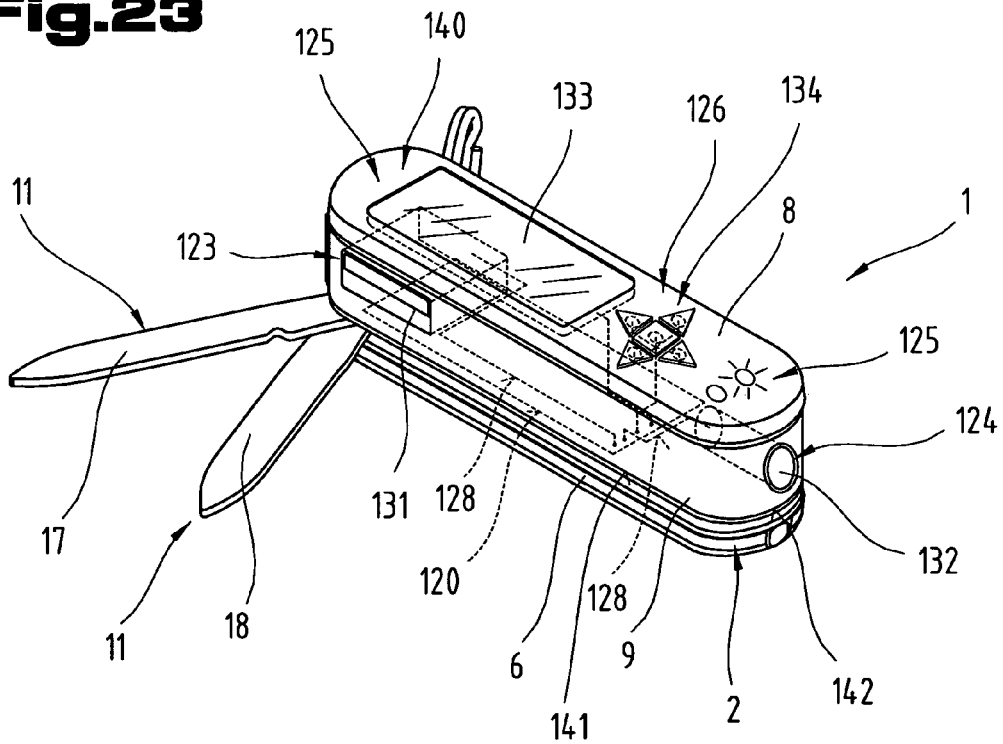
FIG. 23 is a perspective view of anther design variation of the pocket knife, with electronic components integrated in the housing.

FIG. 23 shows another design variation of the pocket tool formed by a pocket knife 1, which comprises at least a first functional component 11 formed by a tool or utensil. In the present design variation, the control circuit 120 and several peripherals 121 are arranged in or on the housing 2 of the pocket knife 1. With the present design variation, the functional components 11 are exclusively formed by utensils or tools such as, for example the knife 1, whereby the control circuit 120 and the peripherals 121 are permanently, i.e. inseparably secured on the housing 2.

In the present exemplified embodiment, the display 133 with a substantially rectangular representation zone 138, is visibly arranged, i.e. exposed on the outer surface 139 of a broad side 140 of the housing 2. The display 133 may be arranged below or within the cover plate 8, whereby the latter is transparent at least in the representation zone 138 of the display 133, or a transparent window made of plastic or glass is inserted in the cover plate 8, or, in another design variation, in the support casing 25 of the other functional component 11. The transparent window or cover plate 8 may form at least by sections an optical magnifying lens for the display 133 disposed underneath.

The data interface 123 is arranged on the narrow side 141 of the housing 2 and, as shown, may form a plug connector socket 131 with electrical contacts, or it may be designed in the form of a male plug element as described for the interface 24, which can be pulled or pivoted out of the receiving area 10. The jack 132 of the input and/or output interface 124 is arranged on the narrow side 141 of the housing 2.

Furthermore, the input elements 134 of the operating system 126 are individually arranged on the broad side 140, the narrow side 141 and, if necessary, on the face side 142 of the housing 2. With the design variation shown, the energy supply system 127 may be permanently integrated in the housing 2 of the pocket tool in the form of an electrical energy storage, particularly battery, whereby for charging the energy storage of the energy supply system 127, electrical energy can be supplied from an external energy source via the data interface 123 or a separate energy supply interface. The external energy source may be formed by a public energy supply mains, whereby a preferably transformed charging or operating voltage can be applied to the energy storage. Furthermore, provision can be made in the housing 2 of the pocket tool for a battery storage compartment not shown in detail, which may be designed for accommodating, for example a cylindrical AA- or AAA-sized battery, or a button cell-type battery.

Figure 24:
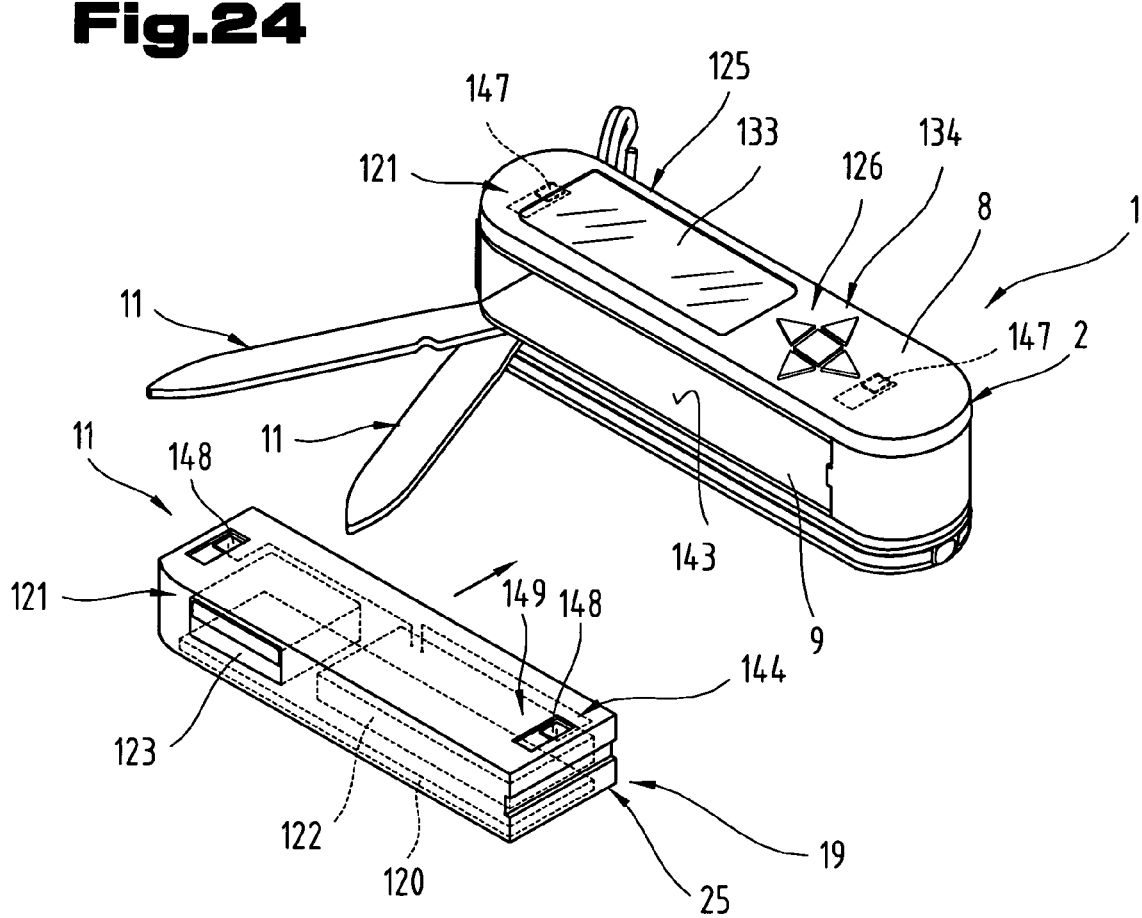
FIG. 24 is a perspective view of another design variation of the pocket knife, with an electronics module detachable from the housing, and with electronic components arranged in the housing of the pocket tool.

FIG. 24 shows another exemplified embodiment of the pocket tool, where the control circuit 120 and/or one or more peripherals 121 are permanently, i.e. inseparably arranged in or on the housing 2, and one or more peripherals 121 and/or the control circuit 120 are arranged on the support casing 25 of the electronics module 19, the latter being detachable from the housing 2 when required.

In the exemplified embodiment shown, the pocket knife 1 has a slot-like module frame 143, into which the modular functional component 11 is linearly inserted and releasably locked by another coupling device 144 via the coupling elements 145, 146, e.g. in the form of elastically yielding, spring-like snap or detent elements, friction elements, or mechanical locking means not shown in detail. An electrically conductive contact element 147 of the signal and/or data bus 128 may be arranged in the region of the housing 2 bordering on said slide-in frame 143 for receiving the module. With the functional component 11 in its storage position, said contact element is in contact with another electrically contact element 148 arranged on the support casing 25 for forming a bus interface 149 of the signal and/or data bus 128. The contact elements 147, 148 may be mutually loaded, for example via spring or frictional force.

Figure 25:
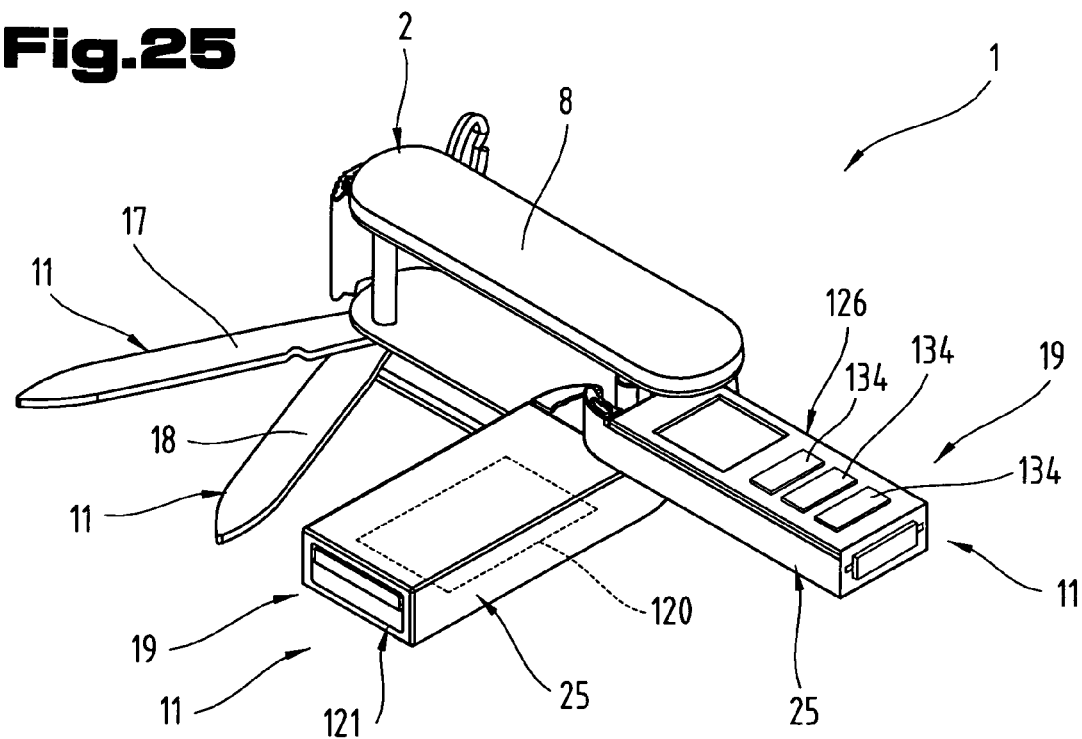
FIG. 25 is a top view of a possible design variation of the pocket knife, with a plate-like electronics module.

FIG. 25 shows another design variation of the pocket tool, where provision is made for several receiving areas 10 for different electronics modules 19, whereby the latter each comprise one or more peripherals 121 and/or the control circuit 120.

As shown by way of example, one of the electronics modules 19 may comprise the operating system 126, which has several input elements 134 on the broad-side wall 26 of the support casing 25. The input elements 134 may be formed in this connection by a keyboard having switching contacts actuated by pressure; a navigation hairline cross or the like. Another electronics module 19 comprises the control circuit 120 and other peripherals 121. It is noted here that particularly the energy supply system 127 formed by an electrical energy storage may form an electronics module 19 on its own. Thus it is possible for the user to have a number of interchangeable electronics modules 19 available, and to exchange such modules as required. In particular, the storage element 122 may form its own electronics module 19, which is found to be beneficial in that the user has to employ in the pocket tool only the storage element 122 containing the information or data the user actually needs at a given time. The individual storage elements 122 may therefore have a lower capacity and a smaller structural size, and several electronics modules 19 with integrated storage elements 122 can be used whenever more storage space is required. If necessary, the control circuit 120 may form its own electronics module 19 as well. A pocket tool with such a modular design can be adapted to individual user requirements with respect to the needed scope of different functions, and individual peripherals 121 or the control circuit 120 can be refitted as required. In addition, provision can be made for different electronics modules 19 with control circuits 120 designed for specific types of information processing, for example in the form of an electronics module 19 for processing audio information; an electronics module 19 for processing video information, or the like, whereby such electronics modules 19 can be designed as individual modules that can be operated in the pocket tool jointly or as individual or discrete units.

The different electronics modules 19 may be connected with each other via the signal and/or data bus 128, which is not shown in FIG. 25 in the interest of superior clarity, whereby said bus may comprise the contact elements 147, 148 or the bus interface 149 described above. Said contact elements may be arranged on the delimiting surface of the receiving area 10; 100 in the housing 2; 95, and on the outer surface 139 of the support casing 25, and are connected to the electrical lines of the signal and/or data bus 128. The lines of the signal and/or data bus 128 may extend in or on the housing 2, for example in the region of the bearing axles 14, on which the functional components 11 are adapted to pivot. In a realizable design variation, a line of the signal and/or data bus 128 is formed by the electrically conductive riveted pin 150. The later may thus form the contact element 147 of the housing 2, said contact element forming the interface 149 for signal and/or data transmission via a contact element 148 provided on the bearing element 36 of the first coupling component 31. For example, provision can be made for two riveted pins 150 to which the positive and negative poles of the energy supply system 127 are connected, whereby the control circuit 120 and the peripherals 121 can be supplied with the required operating voltage via the riveted pins 150. Said circuit and said peripherals are electrically connected to said pins as described below in connection with FIG. 27.

Figure 26:
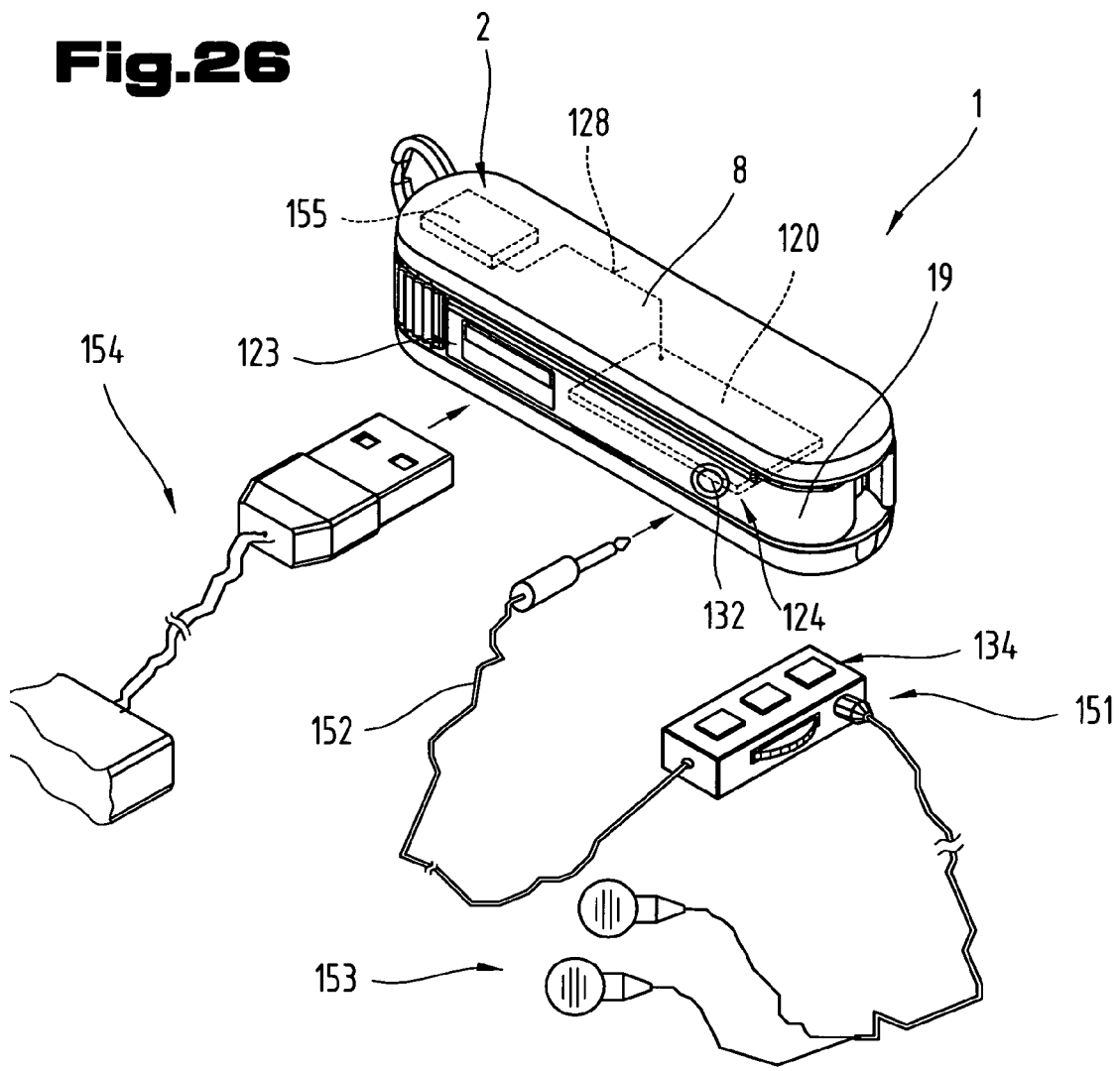
FIG. 26 is a perspective view of another design variation of the pocket knife, with an external controlling unit for controlling the control circuit, and an external data medium.

Another design variation of the pocket tool is shown in FIG. 26, where the housing 2 of the pocket tool comprises the control circuit 120, the data interface 123, the input and/or output interface 124, and, if need be, the storage element 122. The input elements 134 or the operating system 126 for controlling the control circuit 120 are arranged on an external operating unit 151, which is connected to the input and/or output interface 124 via a transmission line 152. On the output side, the operating unit 151 may comprise the loudspeakers 153, in particular earphones or the like.

In the present embodiment, the input elements 136 of the operating system 126 and, if need be, the display 133 (not shown), are arranged on the operating unit 151. Bidirectional signal transmission between the operating unit 151 and the control circuit 120 takes place via the input and/or output interface 124, so that the output signal can be transmitted via the input and/or output interface 124 to the loudspeakers 153, and the control signals of the operating unit 151 can be supplied as input signals to the control circuit 120 via the input and/or output interface 124.

Furthermore, the storage element 122 is shown by way of example in the form of a mass storage 154, which may be formed, for example by a magnetic data medium such as a fixed-disk or optical reading device such as a CD-ROM or DVD-ROM, which can be linked to the control circuit 120 via the data interface 123. Furthermore, a wireless input and/or output interface 124 is shown, which has a transmitter and/or receiver, e.g. a radio, infrared, induction transmitter and/or receiver, via which signals and data can be exchanged with an external device or infrastructure such as a telecommunications or data network. Furthermore, the transmitter and/or receiver may be formed as an FM radio receiver, or as an element for position finding, particularly a navigation transmitter or receiver for the global positioning system (GPS). Another possibility for processing media information has to be mentioned, in connection with which digitized cartographic information stored in the memory is visualized on the display 133, and the actual location of the pocket tool is detected via the element for position finding and displayed on the display 133. If desired, a route can be planned via the pocket tool as well, whereby route or directional data can be output via the input/output device 125.

Figure 27:
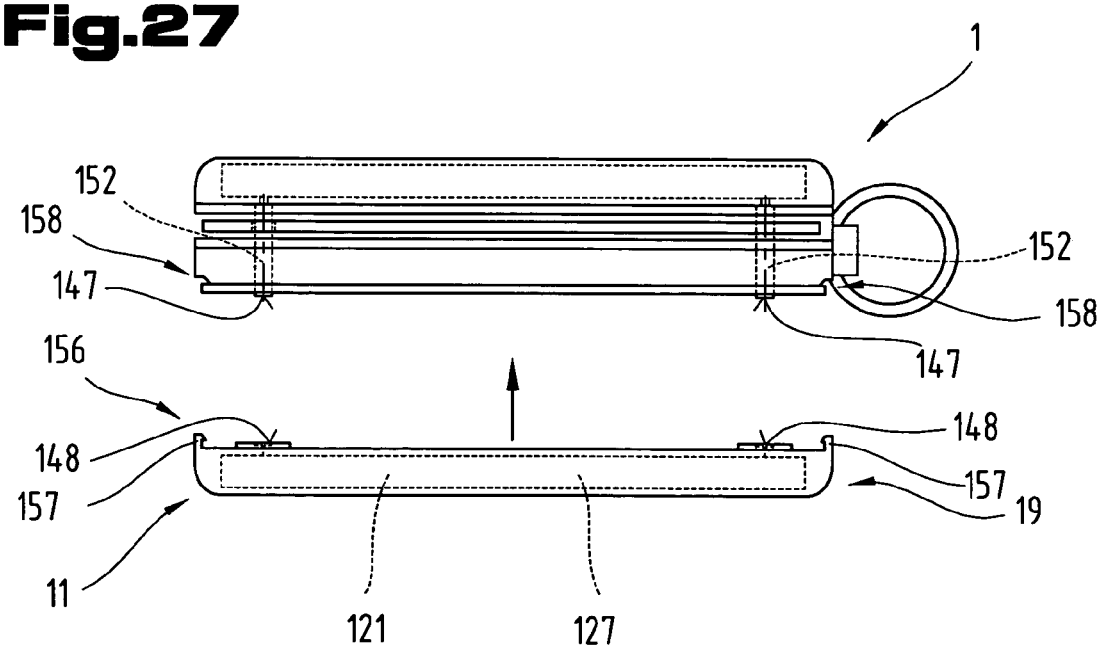
FIG. 27 is a perspective view of yet another design variation of the pocket knife, with a plurality of electronics modules equipped in different ways.

Another design variation of the pocket tool is shown in FIG. 27, whereby one of the electronics modules 19 is substantially plate-shaped and can be mechanically coupled with the housing 2 of the pocket tool via a connection system 156. In the exemplified embodiment shown, the connection system 156 is formed by the snap arms 157 engaging the recesses 158 on the broad side 140 of the housing 2. The functional component 11 can be designed in the form of an outer cover element or cover plate 8 adapted to snap over the side wall 6 of the housing 2, whereby the electrical contact elements 147, 148 can be coupled with the signal and/or data bus 128 arranged in the housing 2. The functional component 11 may particularly comprise the energy supply system 127 formed by the energy storage.

Figure 28:
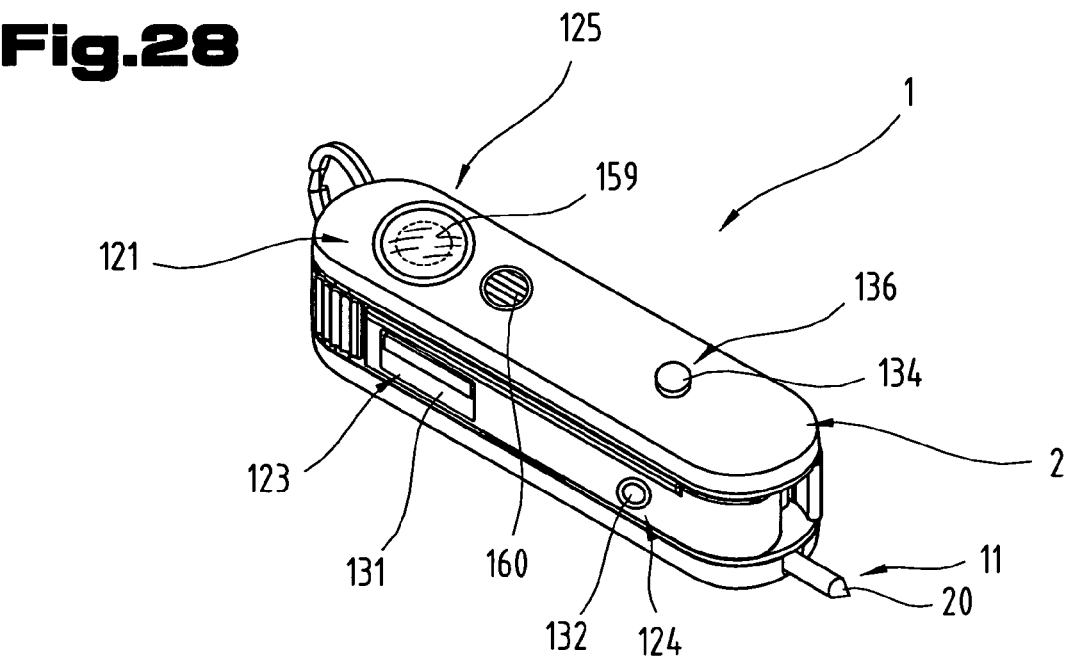
FIG. 28 is a perspective view of yet another design variation of the pocket knife, with input/output devices provided on the cover plate.

FIG. 28 shows yet another design variation of the pocket tool, which comprises an input/output device 125 in the form of a picture detection system 159, particularly a digital camera. Furthermore, an input/output device 125 in the form of a sound pick-up 160, particularly a microphone is shown by way of example. Moreover, an input element 134 of the operating system 126 is arranged on the housing 2 or on the support casing 25, whereby the input element 134 may serve as the trigger for the picture detection system 159 in the form of a camera, or for the sound pick-up 160.

The picture or video information acquired via the picture detection system 159 is or can be stored in the storage element 122 (not shown here in detail), and can be called in via the input/output interface 124 in the analog form, if so required, or in the digital form via the data interface 123. Furthermore, sound information is detectable via the sound pick-up 160, and convertible into the digital form via the control circuit 120 (not shown here in detail), whereby the audio information is or can be stored in the storage element 124.

Figure 29:
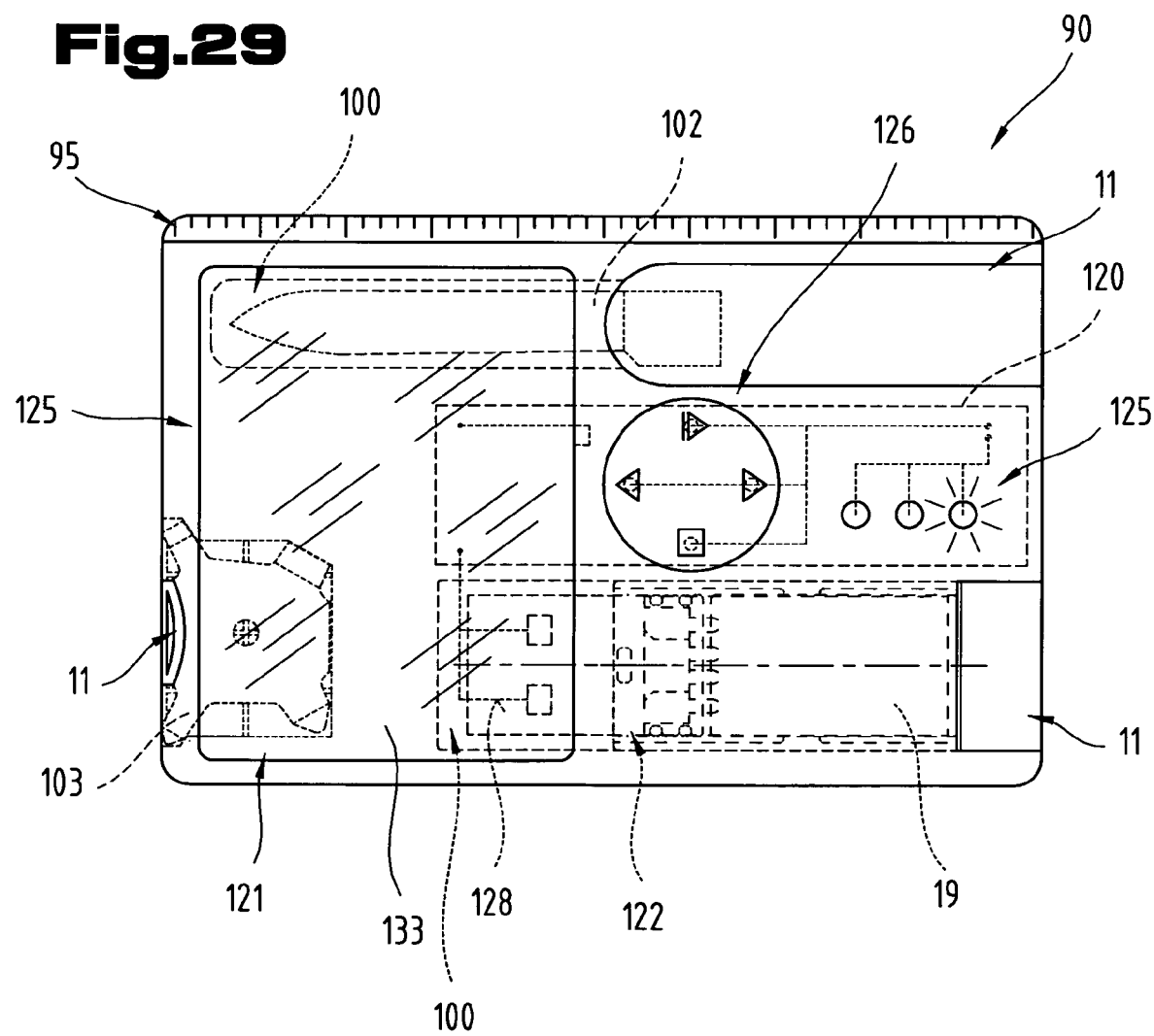
FIG. 29 is a perspective view of a possible design variation of a tool card comprising the electronics module.

FIG. 29 shows yet another design variation of the pocket tool, where the latter is realized in the form of a tool card 90 comprising at least one of the functional components 11. The tool card 90 comprises the control circuit 120, as well as several of the peripherals 121 described above. The structure of the functional components 11 of the tool card 90, and the arrangement of the peripherals 121 in the housing 95 of the tool card 90, or in the support casing 25 of the functional components 11, may correspond with the one described herein above, and is not addressed here in detail.

The exemplified embodiments show possible design variation of the pocket tool, whereby it is noted here that the invention is not limited to any of the design variations specifically shown herein, but that various combinations of the individual design variations among one another are realizable as well, and that in light of the instruction for technical implementation provided by the present invention, such possibilities for different combinations fall within the scope of expertise of the expert skilled and actively engaged in the present technological field. Furthermore, the scope of protection of the present invention jointly covers as well all and any conceivable design variations realizable by combining individual details of the design variations shown and specified herein.

Finally, it is pointed out for the sake of good order that in the interest of superior understanding of the structure of the pocket tool, the latter and its components are to some extent shown untrue to scale and/or enlarged and/or reduced.

Most important of all, the individual embodiments shown in FIGS. 1 to 5; 16 to 18; 19, 20, 21; 22; 23; 24; 25; 26; 27; 28; 29 may represent the object of independent solutions as defined by the invention.

| | LIST OF REFERENCE NUMERALS |
|---|---|
| 1 | Pocket knife |
| 2 | Housing |
| 3 | Width |
| 4 | Length |
| 5 | Receiving body |
| 6 | Side wall |
| 7 | Side surface |
| 8 | Cover plate |
| 9 | Partition |
| 10 | Receiving area |
| 11 | Functional component |
| 12 | End area |
| 13 | End area |
| 14a | Bearing axle |
| 14b | Bearing axle |
| 15a | Bearing axle |
| 15b | Bearing axle |
| 16 | Scissors |
| 17 | Knife |
| 18 | File |
| 19 | Electronics module |
| 20 | Writing pen |
| 21 | Slide |
| 22 | Actuation element |
| 24 | Interface |
| 25 | Support casing |
| 26 | Broad-side wall |
| 27 | Narrow-side wall |
| 28 | Narrow-side wall |
| 29 | Pivot bearing |
| 30 | Coupling device |
| 31 | Coupling component |
| 32 | Coupling component |
| 33 | Longitudinal center axis |
| 34 | Axle |
| 35 | Detent arm |
| 36 | Bearing component |
| 37 | Bearing bush |
| 38 | Bearing surface of first coupling component |
| 39 | Bearing surface of second coupling component |
| 40 | Clamping arm |
| 41 | Receiving slot |
| 42 | Detent nose |
| 43 | Depression |
| 45 | Locking device |
| 46 | Raceway |
| 47 | Holding nose |
| 48 | Radius |
| 50 | Closing cap |
| 51 | Longitudinal axis |
| 52 | Axle |
| 53 | Pivot bearing area |
| 54 | Bearing bore |
| 55 | Stop surface of the closing cap |
| 56 | Stop surface of the bearing axle |
| 57 | Wall element |
| 58 | Stop surface of the closing cap |
| 59 | Wall |
| 60 | End wall element |
| 61 | End wall element |
| 62 | Face edge |
| 62' | Face edge |
| 63 | Support surface |
| 64 | Support surface |
| 65 | Actuation element |
| 66 | Face end |
| 67 | Detent arm |
| 68 | Connection wall |
| 69 | Connection wall |

-continued

LIST OF REFERENCE NUMERALS

| | |
|---|---|
| 70 | Connection wall |
| 71 | Receiving slot |
| 72 | Detent nose |
| 73 | Locking device |
| 74 | Flange |
| 75 | Key ring |
| 76 | Narrow-side wall |
| 77 | Face side |
| 78 | Angle |
| 79 | Pivot bearing area |
| 80 | Bearing bore |
| 81 | Adapter |
| 82 | Plug socket |
| 83 | Arrow |
| 84 | Arrow |
| 85 | Arrow |
| 86 | Arrow |
| 88 | Depression |
| 90 | Tool card |
| 91 | Width |
| 92 | Length |
| 93 | Longitudinal side surface |
| 94 | Transverse side surface |
| 95 | Housing |
| 96 | Base plate |
| 97 | Cover plate |
| 98 | Side surface |
| 99 | Partition |
| 100 | Receiving area |
| 101 | Receiving opening |
| 102 | Knife |
| 103 | Multifunctional tool |
| 105 | Pincers |
| 106 | Phillips screwdriver |
| 107 | Toothpick |
| 108 | Handle |
| 109 | Rule |
| 110 | Longitudinal guide |
| 111 | Guide surface |
| 112 | Side surface |
| 113 | Detent nose |
| 114 | Detent deepening |
| 115 | Memory card |
| 120 | Control circuit |
| 121 | Peripheral |
| 122 | Storage element |
| 123 | Data interface |
| 124 | Input/output interface |
| 125 | Input/output device |
| 126 | Operating system |
| 127 | Energy supply system |
| 128 | Signal and/or data bus |
| 129 | Storage element |
| 130 | Longitudinal guide |
| 131 | Plug socket |
| 132 | Jack |
| 133 | Display |
| 134 | Input element |
| 135 | Key elements |
| 136 | Sliding key |
| 137 | Controller |
| 138 | Representation zone |
| 139 | Outside surface |
| 140 | Broad side |
| 141 | Narrow side |
| 142 | Face side |
| 143 | Module frame |
| 144 | Coupling device |
| 145 | Coupling element |
| 146 | Coupling element |
| 147 | Contact element |
| 148 | Contact element |
| 149 | Bus interface |
| 150 | Riveted pin |
| 151 | Operating unit |
| 152 | Transmission line |
| 153 | Loudspeaker |

-continued

LIST OF REFERENCE NUMERALS

| | |
|---|---|
| 154 | Mass storage |
| 155 | Transmitter and/or receiver |
| 156 | Connection system |
| 157 | Snap arm |
| 158 | Recess |
| 159 | Picture detection system |
| 160 | Sound pick-up |

What is claimed is:

1. A pocket tool, particularly a pocket knife or plate-like tool card, comprising a housing with at least one receiving area, and at least two functional components moveable from a storage position within the receiving area, into a working position outside of the receiving area, of which a first functional component is designed as a tool, particularly a pair of scissors, a knife or a utensil, in particular a toothpick, pincers, cleaning needle, writing pen, wherein a second functional component has a support casing and is equipped with a recordable and readable, nonvolatile memory, as well as an interface; and at least one releasable locking device and a longitudinal guide or a pivot bearing are arranged between the support bearing of the second functional component, and the housing.

2. The pocket tool according to claim 1, wherein the particularly oblong support casing of the second functional component comprises two parallel broad-side walls opposing one another; two parallel narrow-side walls extending substantially vertically between the broad-side walls and opposing one another; as well as two narrow-side walls opposing each other on the face side; and the memory is arranged within the support casing and the interface on one of the narrow-side walls on the face side.

3. The pocket tool according to claim 1, wherein the second functional component has only a part of the length of the housing.

4. The pocket tool according to claim 1, wherein the second functional component is adapted to pivot.

5. The pocket tool according to claim 1, wherein the second functional component is extractable.

6. The pocket tool according to claim 1, wherein the second functional component is separable from the housing.

7. The pocket tool according to claim 1, wherein the pivot bearing is equipped with a coupling device comprising coupling components engageable with and releasable from each other, whereby the support casing is provided with the first coupling component in one of its end areas, and the housing with the second coupling component in one of its face-side end areas.

8. The pocket tool according to claim 7, wherein the second coupling component is formed by a bearing axle, particularly a connection pin immovably arranged in the housing and extending perpendicular to the broad-side walls of the support casing.

9. The pocket tool according to claim 7, wherein the second coupling component is formed by an adapter pivot-mounted on the bearing axle immovably arranged in the housing and extending perpendicular to the broad-side walls of the support casing.

10. The pocket tool according to claim 9, wherein the adapter and the support casing each have at least one plug or detent or snap element; and that the second functional component is releasably connected with the adapter via a plug or detent or snap connection.

11. The pocket tool according to claim 1, wherein the longitudinal guide is formed by the receiving area and delimited at least by sections by at least two side walls and/or partitions arranged spaced from each other, whereby the side walls and for partitions comprise guide surfaces facing one another and extending parallel to each other and parallel to the broad-side and/or narrow-side walls of the support casing.

12. The pocket tool according to claim 1, wherein the longitudinal guide extends parallel to the longitudinal axis of the pocket tool.

13. The pocket tool according to claim 1, wherein the locking device is arranged in the longitudinal expanse of the longitudinal guide.

14. The pocket tool according to claim 1, wherein the locking device has only part of the length of the longitudinal guide.

15. The pocket tool according to claim 1, wherein the locking device is arranged in at least one of the end areas of the longitudinal guide opposing each other.

16. The pocket tool according to claim 1, wherein the locking device is formed by engageable plug, detent or snap elements or friction grip elements arranged on the support casing and in the housing, said elements complementing one another.

17. The pocket tool according to claim 1, wherein the locking device is formed on the coupling components of the coupling device; and that the coupling components each are provided with plug, detent or snap or friction grip elements complementing each other.

18. The pocket tool according to claim 1, wherein the second functional component can be positively and/or non-positively locked via the locking device at least in its storage position within the receiving area.

19. The pocket tool according to claim 1, wherein the housing comprises a receiving body with at least two side walls opposing each other spaced from one another and connected with each other via bearing axles, particularly connection pins, as well as with at least one shaft-like receiving area arranged between the side walls, and with two cover plates secured on the outer surfaces of the side walls facing away from each other; and that the support casing is pivot-mounted on a bearing axle of the housing, swiveling around an axis extending perpendicular to the side surfaces or its broad-side walls.

20. The pocket tool according to claim 1, wherein the housing comprises two flat base and cover plates opposing one another, and, in a plane extending parallel to the base and cover plates, receiving areas for the tool and the second functional component, said receiving areas being separated from one another at least by sections by partitions; and the base and cover plates are forming side surfaces facing each other and extending parallel to the plane at least by sections, and are connected with one another via a connection element.

21. The pocket tool according to claim 19, wherein the two outer side walls and, if required, at least one partition disposed between said walls, are each connected with the receiving body in the end areas of the pocket tool via two bearing axles, particularly connection pins such as riveted pins arranged one on top of the other.

22. The pocket tool according to claim 7, wherein the first coupling component secured on the support casing in the first end area, forms the axle arranged offset relative to the longitudinal center axis of the support casing and extends perpendicular to the side surfaces or broad-side walls of the support casing.

23. The pocket tool according to claim 7, wherein the first coupling component has a detent arm and a bearing component, said detent arm being supported against the second coupling component with its elastically yielding first end zone freely cantilevered on the faceside first end area of the support casing; and said bearing component being guided on the second coupling component via a substantially half-shell-shaped bearing bush arranged coaxially with the second coupling component.

24. The pocket tool according to claim 7, wherein in addition to the first coupling component, the support casing comprises a slightly elastically yielding clamping arm freely cantilevered on the face-side first end area of the support casing, and a receiving slot for receiving the bearing axle, said slot extending between said clamping arm and the detent arm or bearing component (36); and a detent nose protruding into the receiving slot and the bearing axle having the housing form the locking device.

25. The pocket tool according to claim 1, wherein part sections of the housing, particularly of a receiving body or of the base and cover plates, or of the partitions of said plates, form an immovable closing cap allotted to the interface or a second face-side end area of the second functional component; and said interface or the end area of the second functional component, the latter being present in its storage position within the receiving area, are covered by the closing cap at least within the region of its face side facing the closing cap, particularly in the region of the electrical contacts of said interface.

26. The pocket tool according to claim 1, wherein the housing has a closing cap associated with the interface or face side arranged in a second, face-side end area of the support casing, said closing cap being adjustable between an opening and a closing position versus the receiving area; and the interface or end area of the second functional components, when the latter is located in its storage position within the receiving area, is covered by the closing cap at least within the zone of the face side, particularly within the area of its electrical contacts.

27. The pocket tool according to claim 26, wherein the second functional component is pivot-mounted via the pivot bearing on a bearing axle arranged in the first end area of the pocket tool; and the closing cap is pivot-mounted on one of the bearing axles arranged in the second end area of the pocket tool, said second end area opposing the first end area.

28. The pocket tool according to claim 26, wherein the closing cap is approximately sickle-shaped and forms an axle arranged offset versus the longitudinal axis of the pocket tool and extending perpendicular to the side surfaces or broad-side walls of the support casing.

29. The pocket tool according to claim 26, wherein the closing cap comprises a boss-like pivot bearing area with an inner side extending perpendicular to the side surfaces or broad-side walls of the support casing, and a bearing bore supported on the bearing axle, as well as a first stop surface on an inner side facing the receiving area; and that in its closing position, the closing cap is supported with said first stop surface against a stop surface located in the housing.

30. The pocket tool according to claim 26, wherein at least in its closing position, the closing cap is positively and/or nonpositively lockable via an additional locking device.

31. The pocket tool according to claim 26, wherein the closing cap comprises at least one wall element vertically rising at one end of the bearing bore laterally of the longitudinal expanse of said bore, said wall element forming another stop surface, whereby in its opening position, the closing cap is supported with said additional stop surface against the stop surface located in the housing.

32. The pocket tool according to claim 26, wherein the closing cap comprises a circular arc-shaped wall with first and second end wall elements arranged at its ends opposing one another, as well as a detent arm arranged between said end wall element, whereby the first end wall element and the detent arm delimit a receiving slot for receiving the bearing axle, and a detent nose projects into said receiving slot.

33. The pocket tool according to claim 26, wherein the closing cap comprises an actuation element protruding from the outer contour of the housing.

34. The pocket tool according to claim 26, wherein on an outer side facing away from the receiving area, the closing cap is provided with a flange with a through-extending bore; and that a key ring is movably secured on said flange.

35. The pocket tool according to claim 26, wherein a releasable locking device is arranged between the closing cap and the housing, said locking device being formed by the detent nose and the bearing axle.

36. The pocket tool according to claim 26, wherein the closing cap and the housing, particularly the bearing axle comprise engageable plug or detent or snap elements complementing one another.

37. The pocket tool according to claim 35, wherein the locking device is formed by a plug or detent or snap or friction-grip connection.

38. The pocket tool according to claim 1, wherein the memory is formed by a flash memory card.

39. The pocket tool according to claim 1, wherein the memory is formed by a radio frequency identification device (RFID).

40. The pocket tool according to claim 1, wherein the interface is equipped with electrical contacts for reading data in and out of the memory.

41. The pocket tool according to claim 1, wherein the interface is formed by a USB plug connector or USB connector bush or FireWire™ plug connector or FireWire™ connector bush (IEEE 1394).

42. The pocket tool according to claim 1, wherein the interface is formed by a transmitter and/or receiver for wireless data or signal transmission.

43. The pocket tool according to claim 42, wherein the interface is formed by an infrared interface or a radio signal interface.

44. A pocket tool, particularly pocket knife or plate-like tool card, comprising a housing having a first side wall and a second side wall arranged parallel to said first side wall; and an electronics module moveable between a storage position within the housing and a working position outside the housing or can be mechanically coupled with one of the side walls having a support casing; a control circuit; a data memory arranged within the support casing and being connected with said control circuit; a first interface for the data exchange between the memory and an electronic device; a second interface for connecting a sound output device or visual output device to said electronics module; said control circuit being connection to an operating system formed for controlling the volume and for selecting a data object stored in said memory, said control circuit having a control means assigned to said control circuit and for processing digitized media information for example electronic audio, picture or video data stored in said memory.

45. The pocket tool according to claim 44, wherein the second functional component movable from a storage position within the receiving area, into a working position outside of the receiving area, and having the particularly oblong and substantially rectangular support casing, is equipped with the control circuit and for the at least one peripheral.

46. The pocket tool according to claim 45, wherein at least one releasable locking device and a longitudinal guide or a pivot bearing are arranged between the support casing of the second functional component, and the housing.

47. The pocket tool according to claim 45, wherein the particularly oblong support casing of the movable functional component comprises two parallel broad-side walls opposing one another; two parallel narrow-side walls extending substantially vertically between the broad-side walls and opposing one another; as well as two narrow-side walls opposing each other on the face side; and the memory is arranged within the support casing and the data interface on one of the narrow-side walls on the face side.

48. The pocket tool according to claim 45, wherein the second functional component has only a part of the length of the housing.

49. The pocket tool according to claim 45, wherein the movable functional component is adapted to pivot.

50. The pocket tool according to claim 45, wherein the movable functional component is extractable.

51. The pocket tool according to claim 45, wherein the movable functional component is separable from the housing.

52. The pocket tool according to claim 46, wherein the pivot bearing is equipped with a coupling device comprising coupling components engageable with and releasable from each other, whereby the support casing is provided with the first coupling component in one of its end areas, and the housing with the second coupling component in one of its face-side end areas.

53. The pocket tool according to claim 46, wherein the longitudinal guide is formed by the receiving area and delimited at least by sections by at least two side walls and for partitions arranged spaced from each other, whereby the side walls and/or partitions comprise guide surfaces facing one another and extending parallel to each other and parallel to the broad-side and/or narrow-side walls of the support casing.

54. The pocket tool according to claim 46, wherein the longitudinal guide extends parallel to the longitudinal axis of the pocket tool.

55. The pocket tool according to claim 46, wherein the locking device is arranged in the longitudinal expanse of the longitudinal guide.

56. The pocket tool according to claim 46, wherein the locking device has only part of the length of the longitudinal guide.

57. The pocket tool according to claim 46, wherein the locking device is arranged in at least one of the end areas of the longitudinal guide opposing each other.

58. The pocket tool according to claim 46, wherein the locking device is formed by engageable plug, detent or snap elements or friction grip elements arranged on the support casing and in the housing, said elements complementing one another.

59. The pocket tool according to claim 46, wherein the locking device is formed on the coupling components of the coupling device; and the coupling components each are provided with plug, detent or snap or friction grip elements complementing each other.

60. The pocket tool according to claim 45, wherein the movable functional component can be positively and/or nonpositively locked via the locking device at least in its storage position within the receiving area.

61. The pocket tool according to claim 44, wherein the housing comprises a receiving body with at least two side walls opposing each other spaced from one another and connected with each other via bearing axles, particularly connection pins, as well as with at least one shaft-like receiving area arranged between the side walls, and with two cover plates secured on the outer surfaces of the side walls facing away from each other; and the support casing is pivot-mounted on one of the bearing axles of the housing, swiveling around an axis extending perpendicular to the side surfaces or its broad-side walls.

62. The pocket tool according to claim 44, wherein the housing comprises two flat base and cover plates opposing one another, and, in a plane extending parallel to the base and cover plates, receiving areas for the tool and the second functional component, said receiving areas being separated from one another at least by sections by partitions; and the base and cover plates are forming side surfaces facing each other and extending parallel to the plane at least by sections, and are connected with one another via a connection element.

63. The pocket tool according to claim 61, wherein the two outer side walls and, if required, at least one partition disposed between said walls, are each connected with the receiving body in the end areas of the pocket tool via two bearing axles, particularly connection pins such as riveted pins arranged one on top of the other.

64. The pocket tool according to claim 52, wherein the first coupling component secured on the support casing in the first end area, forms the axle arranged offset relative to the longitudinal center axis of the support casing and extends perpendicular to the side surfaces or broad-side walls of the support casing.

65. The pocket tool according to claim 52, wherein the first coupling component has a detent arm and a bearing component, said detent arm being supported against the second coupling component with its elastically yielding first end zone freely cantilevered on the faceside first end area of the support casing; and said bearing component being guided on the second coupling component via a substantially half-shell-shaped bearing bush arranged coaxially with the second coupling component.

66. The pocket tool according to claim 52, wherein in addition to the first coupling component, the support casing comprises a slightly elastically yielding clamping arm freely cantilevered on the face-side first end area of the support casing, and a receiving slot for receiving the bearing axle, said slot extending between said clamping arm and the detent arm or bearing component; and a detent nose protruding into the receiving slot and the bearing axle having the housing form the locking device.

67. The pocket tool according to claim 44, wherein part sections of the housing, particularly of a receiving body or of the base and cover plates, or of the partitions of said plates, form an immovable closing cap allotted to the data interface or a second face-side end area of the second functional component; and said data interface or the end area of the movable functional component, the latter being present in its storage position within the receiving area, are covered by the closing cap at least within the region of its face side facing the closing cap, particularly in the region of the electrical contacts of said interface.

68. The pocket tool according to claim 44, wherein the housing has a closing cap associated with the data interface or face side arranged in a second, face-side end area of the support casing, said closing cap being adjustable between an opening and a closing position versus the receiving area; and that the data interface or end area of the movable functional component, when the latter is located in its storage position within the receiving area, is covered by the closing cap at least within the zone of the face side, particularly within the area of its electrical contacts.

69. The pocket tool according to claim 68, wherein the movable functional component is pivot-mounted via the pivot bearing on a bearing axle arranged in the first end area of the pocket tool; and the closing cap is pivot-mounted on one of the bearing axles arranged in the second end area of the pocket tool, said second end area opposing the first end area.

70. The pocket tool according to claim 68, wherein the closing cap is approximately sickle-shaped and forms an axle arranged offset versus the longitudinal axis of the pocket tool and extending perpendicular to the side surfaces or broad-side walls of the support casing.

71. The pocket tool according to claim 68, wherein the closing cap comprises a boss-like pivot bearing area with an inner side extending perpendicular to the side surfaces or broad-side walls of the support casing, and a bearing bore supported on the bearing axle, as well as a first stop surface on an inner side facing the receiving area; and in its closing position, the closing cap is supported with said first stop surface against a stop surface located in the housing.

72. The pocket tool according to claim 68, wherein at least in its closing position, the closing cap is positively and/or nonpositively lockable via an additional locking device.

73. The pocket tool according to claim 68, wherein the closing cap comprises at least one wall element vertically rising at one end of the bearing bore laterally of the longitudinal expanse of said bore, said wall element forming another stop surface, whereby in its opening position, the closing cap is supported with said additional stop surface against the stop surface located in the housing.

74. The pocket tool according to claim 68, wherein the closing cap comprises a circular arc-shaped wall with first and second end wall elements arranged at its ends opposing one another, as well as a detent arm arranged between said end wall element, whereby the first end wall element and the detent arm delimit a receiving slot for receiving the bearing axle, and a detent nose projects into said receiving slot.

75. The pocket tool according to claim 68, wherein the closing cap comprises an actuation element protruding from the outer contour of the housing.

76. The pocket tool according to claim 68, wherein on an outer side facing away from the receiving area, the closing cap is provided with a flange with a through-extending 85-bore; and a key ring is movably secured on said flange.

77. The pocket tool according to claim 68, wherein a releasable locking device is arranged between the closing cap and the housing, said locking device being formed by the detent nose and the bearing axle.

78. The pocket tool according to claim 68, wherein the closing cap and the housing, particularly the bearing axle comprise engageable plug or detent or snap elements complementing one another.

79. The pocket tool according to claim 77, wherein the locking device is formed by a plug or detent or snap or friction-grip connection.

80. The pocket tool according to claim 44, wherein the memory, particularly the storage element, is formed by a flash memory card.

81. The pocket tool according to claim 44, wherein the memory, particularly the storage element, is formed by a radio frequency identification device (RFID).

82. The pocket tool according to claim 44, wherein the data interface is equipped with electrical contacts for reading data in and out of the memory.

83. The pocket tool according to claim 44, wherein the data interface is formed by a USB plug connector or USB connector bush or FireWire™ plug connector or FireWire™ connector bush (IEEE 1394).

84. The pocket tool according to claim 44, wherein the data interface is formed by a transmitter and/or receiver for wireless data or signal transmission.

85. The pocket tool according to claim 84, wherein the data interface is formed by an infrared or radio signal interface.

86. The pocket tool according to claim 44, wherein the digitized media information is stored in the first storage element or on an external data medium connected with the data interface.

87. The pocket tool according to claim 44, wherein the control circuit is formed by a computer structure comprising at least one processor unit, an input/output system and a system bus.

88. The pocket tool according to claim 87, wherein one or more of the peripherals are linked with the input/output system of the control circuit.

89. The pocket tool according to claim 44, wherein a control means of the control circuit is designed for converting the digital media information stored in the memory into transmittable, particularly analog output signals.

90. The pocket tool according to claim 89, wherein the control means is formed by a control logic storable as software in a main memory of the processor unit.

91. The pocket tool according to claim 44, wherein the control circuit comprises an additional digital storage element with a read-only memory, particularly an erasable and programmable flash EPROM or EEPROM memory, in which the control logic is stored in the form of a preferably unchangeable initial program loader.

92. The pocket tool according to claim 44, wherein the digitized media information is stored in the memory in the coded or compressed form, for example as an MPEG-1 Layer 3 (Movie Pictures Experts Group) or WMA (windows Media Audio) data file.

93. The pocket tool according to claim 90, wherein the control logic of the control circuit comprises a coding and/or decoding routine for processing digitized media information, particularly MP3 or WMA data files.

94. The pocket tool according to claim 44, wherein the peripherals and the control circuit are linked via a signal and/or data bus arranged in the housing.

95. The pocket tool according to claim 94, wherein the signal and/or data bus comprises at least one bus interface with a first contact element on the housing; and an additional contact element is arranged on the support casing of the additional functional component, said additional contact element corresponding with the first contact element when said 88-functional component is in the storage position in the housing.

96. The pocket tool according to claim 94, wherein the electrical lines of the signal and/or data bus are arranged in the side walls and partitions of the cover plates or base plate of the housing; and contact elements of the signal and/or data bus connected to said lines are arranged freely accessible or exposed in the housing in the receiving areas.

97. The pocket tool according to claim 94, wherein electrical lines of the signal and/or data bus are formed by the electrically conductive riveted pins connecting the side walls and partitions to form a receiving body.

98. The pocket tool according to claim 44, wherein one of the peripherals is formed by a particularly analog input and/or output interface where electrical signals, for example audio and/or video signals are input or output.

99. The pocket tool according to claim 98, wherein the input and/or output interface comprises a jack, for example a headphone or microphone jack, and/or a video input and output.

100. The pocket tool according to claim 44, wherein an input and/or output interface of the peripheral and/or the data interface are formed by a wireless transmitter and/or receiver, particularly a radio, infrared or induction transmitter and receiver.

101. The pocket tool according to claim 44, wherein one of the peripherals is formed by a sound and/or visual input and/or output device, for example by a display and/or picture detection system.

102. The pocket tool according to claim 101, wherein the visual input and/or output device is formed by a display, for example by a graphics display or light sources such as LED'S, or by a picture detection system, for example a digital camera.

103. The pocket tool according to claim 101, wherein the sound input and/or output device is formed by a loudspeaker or a sound pick-up, particularly a microphone.

104. The pocket tool according to claim 44, wherein one of the peripherals is formed by an operating system with one or more input elements for setting operating parameters and operating conditions of the control circuit.

105. The pocket tool according to claim 104, wherein at least one input element is formed by a switching contact electrically coupled to the control circuit, for example a key element or a slide element; or the input element is formed by an infinitely variable controller, e.g. a potentiometer.

106. The pocket tool according to claim 104, wherein an operating surface, for example a menu control visualized on the display, is associated with the operating system, said display being adapted to being navigated via the input elements.

107. The pocket tool according to claim 44, wherein one of the peripherals is formed by an electric position detection system, particularly a touch screen forming in one common physical unit the display and the operating system.

108. The pocket tool according to claim 44, wherein the data interface and/or the input elements of the operating system, and/or the jack of the input and/or output interface are arranged and accessible on one of the broad-side walls and/or one of the narrow-side walls of the support casing of the movable second functional component.

109. The pocket tool according to claim 45, wherein an exposed representation zone of the display, said zone being visible from the outside, is arranged on one of the broadside walls of the support casing.

110. The pocket tool according to claim 101, wherein the display and/or at least one input element are arranged in or on the housing, particularly above, within or below the cover plate or the base plate.

111. The pocket tool according to claim 44, wherein one of the peripherals is formed by an electrical energy supply system.

112. The pocket tool according to claim 111, wherein the energy supply system is formed by a self-sufficient energy storage, particularly a preferably rechargeable battery arranged or arrangeable within the housing or the support casing of a functional component.

113. The pocket tool according to claim 111, wherein the energy supply system is formed by the electrical conductors in the signal and/or data bus, the latter being connectable to an external energy source.

114. The pocket tool according to claim 44, wherein the control circuit and/or the at least one peripheral are integrated in the housing.

115. The pocket tool according to claim 45, wherein several peripherals are arranged in the second functional component and/or in an additional functional component.

116. A pocket tool comprising:
a) a housing having;
  (1) a first side wall (6);
  (2) a second side wall (6) arranged parallel to said first side wall;
  (3) a first bearing axle (14a);
  (4) a second bearing axle (14b), said first and second bearing axles arranged in one end area of said housing and one above the other, and extending between said first and second side walls;
b) at least one receiving area arranged between the first and second side walls;
c) a functional component pivotably mounted on said first bearing axle by means of a bearing component (36) and movable between a storage position within the receiving area and a working position outside of the receiving area, said bearing component having: (1) an axle (34) arranged offset relative to a longitudinal center axis (33) of the functional component and extends perpendicular to the side walls;
said functional component further having a clamping arm (40) which engages with second bearing axle when said functional component is moved in its storage position within the receiving area; and
a slot is arranged between the bearing component and clamping arm and adapted for receiving the second bearing axle.

117. The pocket tool of claim 1, wherein the housing has a first receiving area, and a second receiving area, and the first functional component is moveable between a storage position within the first receiving area and a working position at least partly outside the first receiving area, and the second functional component moveable between a storage position within the second receiving area and a working position outside the second receiving area.

118. The pocket tool of claim 1, wherein the interface is for data exchange between the memory and an external electronic device.

* * * * *